(12) United States Patent
Fan et al.

(10) Patent No.: US 10,698,479 B2
(45) Date of Patent: Jun. 30, 2020

(54) METHOD FOR STARTING EYE TRACKING FUNCTION AND MOBILE DEVICE

(71) Applicant: Huawei Technologies Co., Ltd., Shenzhen (CN)

(72) Inventors: Shunan Fan, Beijing (CN); Wenmei Gao, Beijing (CN); Zhuo Wei, Singapore (SG)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 102 days.

(21) Appl. No.: 15/764,745

(22) PCT Filed: Sep. 30, 2015

(86) PCT No.: PCT/CN2015/091312
§ 371 (c)(1),
(2) Date: Mar. 29, 2018

(87) PCT Pub. No.: WO2017/054196
PCT Pub. Date: Apr. 6, 2017

(65) Prior Publication Data
US 2018/0284887 A1    Oct. 4, 2018

(51) Int. Cl.
*G06F 3/01* (2006.01)
*G06F 3/038* (2013.01)
*A61B 3/113* (2006.01)
*G02B 27/00* (2006.01)

(52) U.S. Cl.
CPC .............. *G06F 3/013* (2013.01); *A61B 3/113* (2013.01); *G06F 3/038* (2013.01); *G02B 27/0093* (2013.01)

(58) Field of Classification Search
CPC ..... G06F 3/013; G06F 3/038; G02B 27/0093; A61B 3/113
See application file for complete search history.

(56) References Cited

U.S. PATENT DOCUMENTS

| | | | |
|---|---|---|---|
| 6,734,845 | B1 | 5/2004 | Nielsen et al. |
| 8,594,374 | B1 | 11/2013 | Bozarth |
| 2012/0257035 | A1 | 10/2012 | Larsen |
| 2013/0135196 | A1 | 5/2013 | Park et al. |
| 2014/0313307 | A1 | 10/2014 | Oh et al. |
| 2015/0066980 | A1 | 3/2015 | Kim |

(Continued)

FOREIGN PATENT DOCUMENTS

| | | |
|---|---|---|
| CN | 102749990 A | 10/2012 |
| CN | 102981620 A | 3/2013 |

(Continued)

OTHER PUBLICATIONS

Hayashi, E., et al.,"CASA: Context-Aware Scalable Authentication," XP055483104, Proceedings of the Ninth Symposium on Usable Privacy and Security Soup, Jul. 24, 2013, 10 pages.

(Continued)

*Primary Examiner* — Jack Dinh
(74) *Attorney, Agent, or Firm* — Conley Rose, P.C.

(57) ABSTRACT

A method includes determining that a mobile device is in a preset scenario, starting at least one monitor, detecting that an eye of a user has entered a monitoring area of the at least one monitor, enabling an eye tracking mode, collecting a first gaze action of the eye whose duration is not less than a first preset threshold, and starting the eye tracking function.

20 Claims, 20 Drawing Sheets

(56) References Cited

U.S. PATENT DOCUMENTS

2015/0268719 A1   9/2015  Li
2016/0093113 A1   3/2016  Liu et al.

FOREIGN PATENT DOCUMENTS

| CN | 103135762 A | 6/2013 |
|---|---|---|
| CN | 103616953 A | 3/2014 |
| CN | 104391567 A | 3/2015 |
| CN | 104391572 A | 3/2015 |
| CN | 104423585 A | 3/2015 |
| CN | 104836900 A | 8/2015 |
| WO | 2011083092 A1 | 7/2011 |

OTHER PUBLICATIONS

Foreign Communication From a Counterpart Application, European Application No. 15905108.5, Extended European Search Report dated Jun. 19, 2018, 9 pages.
Machine Translation and Abstract of Chinese Publication No. CN102981620, Mar. 20, 2013, 12 pages.
Machine Translation and Abstract of Chinese Publication No. CN103616953, Mar. 5, 2014, 16 pages.
Foreign Communication From a Counterpart Application, PCT Application No. PCT/CN2015/091312, English Translation of International Search Report dated May 18, 2016, 3 pages.
Foreign Communication From a Counterpart Application, PCT Application No. PCT/CN2015/091312, English Translation of Written Opinion dated May 18, 2016, 5 pages.
Machine Translation and Abstract of Chinese Publication No. CN104836900, Aug. 12, 2015, 22 pages.
Foreign Communication From a Counterpart Application, Chinese Application No. 201580082932.8, Chinese Office Action dated May 28, 2019, 9 pages.

METHOD FOR STARTING EYE TRACKING FUNCTION AND MOBILE DEVICE

CROSS-REFERENCE TO RELATED APPLICATION

This application is a U.S. National Stage of International Patent Application No. PCT/CN2015/091312 filed Sep. 30, 2015, which is hereby incorporated by reference in its entirety.

TECHNICAL FIELD

The present disclosure relates to the communications field, and in particular, to a method for starting an eye tracking function and a mobile device.

BACKGROUND

An eye tracking technology is a technology involving applications of science. A first application is to perform tracking according to feature changes of an eye and eye surroundings. A second application is to perform tracking according to changes of an iris angle. A third application is to extract features by proactively projecting a beam, such as an infrared ray, onto an iris. Application of the eye tracking technology to mobile devices is used as example. Currently, the eye tracking technology used in a mobile device is mainly applied to operations such as collecting a user's interests, unlocking a screen lock, and determining whether a user is looking at the mobile device or scrolling a display.

However, when the user is inconvenient to operate the mobile device manually (for example, the user is in a meeting, or both hands of the user are being occupied), the user may be unable to start an eye tracking function. Consequently, the user cannot use the mobile device to complete a related service. This is poorly convenient.

SUMMARY

Embodiments of the present disclosure provide a method for starting an eye tracking function and a mobile device such that a mobile device can start by itself an eye tracking function, making it more convenient for a user to use the mobile device.

To achieve the foregoing objective, the embodiments of the present disclosure use the following technical solutions.

According to a first aspect, an embodiment of the present disclosure provides a method for starting an eye tracking function, where the method is applied to a mobile device having an eye tracking function, and includes determining that the mobile device is in a preset scenario, and starting at least one monitor, detecting that an eye of a user has entered a monitoring area of the at least one monitor, enabling an eye tracking mode, collecting a first gaze action of the eye whose duration is not less than a first preset threshold, and starting the eye tracking function, where the first gaze action is used to start the eye tracking function.

In a first possible implementation of the first aspect, before starting a first monitor, the method further includes obtaining a straight line distance between the eye and each monitor of the mobile device, and determining a monitor at a shortest straight line distance as a to-be-started monitor.

With reference to the first aspect or the first possible implementation of the first aspect, in a second possible implementation of the first aspect, after starting the eye tracking function, the method further includes displaying an interaction screen.

According to the second possible implementation of the first aspect, in a third possible implementation of the first aspect, before displaying an interaction screen, the method further includes starting a monitor that is not started.

According to the third possible implementation of the first aspect, in a fourth possible implementation of the first aspect, after starting a monitor that is not started, and before displaying an interaction screen, the method further includes determining whether a screen lock needs to be unlocked, displaying a lock screen if the screen lock needs to be unlocked, collecting a second gaze action of the eye, and unlocking the screen lock if the second gaze action is the same as a first preset unlock action.

According to the fourth possible implementation of the first aspect, in a fifth possible implementation of the first aspect, determining whether a screen lock needs to be unlocked includes determining whether the mobile device is in a secure state, where the secure state means that geographical location information of the mobile device is the same as preset geographical location information, or that a distance between the mobile device and a wearable device is not greater than a second preset threshold and a wireless connection has been established between the wearable device and the mobile device, and determining that the screen lock does not need to be unlocked if the mobile device is in the secure state.

According to any one of the second possible implementation of the first aspect to the fifth possible implementation of the first aspect, in a sixth possible implementation of the first aspect, after displaying an interaction screen, the method further includes collecting a third gaze action of the eye, where the third gaze action is used to trigger start of an application on the mobile device, and starting the application according to the third gaze action.

According to the sixth possible implementation of the first aspect, in a seventh possible implementation of the first aspect, after starting the application, the method further includes collecting a close action of the eye, where the close action is used to trigger disabling of the eye tracking mode, and disabling the eye tracking mode according to the close action.

According to the sixth possible implementation of the first aspect, in an eighth possible implementation of the first aspect, after starting the application, the method further includes receiving an instruction entered by the user, and disabling the eye tracking mode according to the instruction.

In a ninth possible implementation of the first aspect, the preset scenario is a scenario in which the mobile device receives a notification message in a screen off state, a scenario in which the mobile device is laid flat and receives no operation, or a scenario in which the user wakes up the mobile device using voice.

According to a second aspect, an embodiment of the present disclosure provides a mobile device, where the mobile device has an eye tracking function and the mobile device contains at least one monitor, and the mobile device includes a determining unit configured to determine that the mobile device is in a preset scenario, an on/off unit configured to start at least one monitor when the determining unit determines that the mobile device is in the preset scenario, a monitoring unit configured to monitor whether an eye of a user has entered a monitoring area of the at least one monitor, where the on/off unit is further configured to enable an eye tracking mode if the monitoring unit detects that the eye of the user has entered the monitoring area of the at least one monitor, and a collection unit configured to collect a first gaze action of the eye, where the on/off unit is further configured to start the eye tracking function if the collection unit collects a first gaze action of the eye whose duration is not less than a first preset threshold, where the first gaze action is used to start the eye tracking function.

In a first possible implementation of the second aspect, the mobile device further includes an obtaining unit, where the obtaining unit is configured to obtain a straight line distance between the eye and each monitor of the mobile device, and the determining unit is further configured to determine a monitor at a shortest straight line distance obtained by the obtaining unit, as a to-be-started monitor.

With reference to the second aspect or the first possible implementation of the second aspect, in a second possible implementation of the second aspect, the mobile device further includes a display unit, where the display unit is configured to display an interaction screen after the on/off unit starts the eye tracking function.

According to the second possible implementation of the second aspect, in a third possible implementation of the second aspect, the on/off unit is further configured to start a monitor that is not started before the display unit displays the interaction screen.

According to the third possible implementation of the second aspect, in a fourth possible implementation of the second aspect, the mobile device further includes a judgment unit, where the judgment unit is configured to determine whether a screen lock needs to be unlocked after the on/off unit starts the monitor that is not started and before the display unit displays the interaction screen, the display unit is further configured to display a lock screen if the judgment unit determines that the screen lock needs to be unlocked, the collection unit is further configured to collect a second gaze action of the eye, and the judgment unit is further configured to determine whether the second gaze action collected by the collection unit is the same as a first preset unlock action, and the mobile device further includes a processing unit, where the processing unit is configured to unlock the screen lock if the judgment unit determines that the second gaze action is the same as the first preset unlock action.

According to the fourth possible implementation of the second aspect, in a fifth possible implementation of the second aspect, the judgment unit is further configured to determine whether the mobile device is in a secure state, where the secure state means that geographical location information of the mobile device is the same as preset geographical location information, or that a distance between the mobile device and a wearable device is not greater than a second preset threshold and a wireless connection has been established between the wearable device and the mobile device, and the determining unit is further configured to determine that the screen lock does not need to be unlocked if the judgment unit determines that the mobile device is in the secure state.

According to the second possible implementation of the second aspect or the fifth possible implementation of the second aspect, in a sixth possible implementation of the second aspect, the collection unit is further configured to collect a third gaze action of the eye after the display unit displays the interaction screen, where the third gaze action is used to trigger start of an application on the mobile device, and the on/off unit is further configured to start the application according to the third gaze action collected by the collection unit.

According to the sixth possible implementation of the second aspect, in a seventh possible implementation of the second aspect, the collection unit is further configured to collect a close action of the eye after the on/off unit starts the application, where the close action is used to trigger disabling of the eye tracking mode, and the on/off unit is further configured to disable the eye tracking mode according to the close action collected by the collection unit.

According to the sixth possible implementation of the second aspect, in an eighth possible implementation of the second aspect, the mobile device further includes a receiving unit, where the receiving unit is configured to receive an instruction entered by the user, and the on/off unit is further configured to disable the eye tracking mode according to the instruction received by the receiving unit.

In a ninth possible implementation of the second aspect, the preset scenario is a scenario in which the mobile device receives a notification message in a screen off state, a scenario in which the mobile device is laid flat and receives no operation, or a scenario in which the user wakes up the mobile device using voice.

According to a third aspect, an embodiment of the present disclosure provides a mobile device, where the mobile device has an eye tracking function and the mobile device contains at least one monitor, and the mobile device includes a processor, where the processor is configured to determine that the mobile device is in a preset scenario, and start at least one monitor, detect that an eye of a user has entered a monitoring area of the at least one monitor, and enable an eye tracking mode, collect a first gaze action of the eye whose duration is not less than a first preset threshold, and start the eye tracking function, where the first gaze action is used to start the eye tracking function.

In a first possible implementation of the third aspect, the processor is further configured to obtain a straight line distance between the eye and each monitor of the mobile device, and determine a monitor at a shortest straight line distance as a to-be-started monitor.

With reference to the third aspect or the first possible implementation of the third aspect, in a second possible implementation of the third aspect, the mobile device further includes a display, where the display is configured to display an interaction screen after the processor starts the eye tracking function.

According to the second possible implementation of the third aspect, in a third possible implementation of the third aspect, the processor is further configured to start a monitor that is not started before the display displays the interaction screen.

According to the third possible implementation of the third aspect, in a fourth possible implementation of the third aspect, after starting the monitor that is not started and before the display displays the interaction screen, the processor is further configured to determine whether a screen lock needs to be unlocked, determine that the screen lock needs to be unlocked, trigger the display to display a lock screen, collect a second gaze action of the eye, determine whether the second gaze action is the same as a first preset unlock action, and unlock the screen lock if the second gaze action is the same as the first preset unlock action.

According to the fourth possible implementation of the third aspect, in a fifth possible implementation of the third aspect, the processor is further configured to determine whether the mobile device is in a secure state, where the secure state means that geographical location information of the mobile device is the same as preset geographical location information, or that a distance between the mobile device and a wearable device is not greater than a second preset threshold and a wireless connection has been established between the wearable device and the mobile device, and determine that the screen lock does not need to be unlocked if the mobile device is in the secure state.

According to any one of the second possible implementation of the third aspect to the fifth possible implementation of the third aspect, in a sixth possible implementation of the third aspect, the processor is further configured to collect a third gaze action of the eye after the display displays the interaction screen, where the third gaze action is used to trigger start of an application on the mobile device, and start the application according to the third gaze action.

According to the sixth possible implementation of the third aspect, in a seventh possible implementation of the third aspect, the processor is further configured to collect a close action of the eye after starting the application, where the close action is used to trigger disabling of the eye tracking mode, and disable the eye tracking mode according to the close action.

According to the sixth possible implementation of the third aspect, in an eighth possible implementation of the third aspect, the processor is further configured to receive an instruction entered by the user, and disable the eye tracking mode according to the received instruction.

In a ninth possible implementation of the third aspect, the preset scenario is a scenario in which the mobile device receives a notification message in a screen off state, a scenario in which the mobile device is laid flat and receives no operation, or a scenario in which the user wakes up the mobile device using voice.

According to a fourth aspect, an embodiment of the present disclosure provides a readable storage medium, including one or more programs, and when a mobile device executes the program, the mobile device executes the method according to any possible implementation of the first aspect.

The embodiments of the present disclosure provide a method for starting an eye tracking function and a mobile device, and the method is applied to a mobile device having an eye tracking function. When determining that the mobile device is in a preset scenario, the mobile device starts at least one monitor, and when detecting that an eye of a user has entered a monitoring area of the at least one monitor, the mobile device enables an eye tracking mode. After the eye tracking mode is enabled, if the mobile device collects a first gaze action of the eye whose duration is not less than a first preset threshold, the mobile device starts the eye tracking function.

According to this solution, in a condition of the preset scenario, the mobile device can enable the eye tracking mode when detecting, using the at least one monitor, that the eye of the user has entered the monitoring area of the at least one monitor. Further, after the eye tracking mode is enabled, if the mobile device collects, using the at least one monitor, the first gaze action of the eye whose duration is not less than the first preset threshold, the mobile device starts the eye tracking function. This avoids a problem of poor convenience that, in the condition of the preset scenario, a user cannot use, before the user starts an eye tracking function manually, the eye tracking function of a mobile device to complete a related service. The present disclosure implements that the mobile device starts by itself the eye tracking function, making it more convenient for the user to use the mobile device.

BRIEF DESCRIPTION OF DRAWINGS

To describe the technical solutions in the embodiments of the present disclosure more clearly, the following briefly describes the accompanying drawings required for describing the embodiments. The accompanying drawings in the following description show merely some embodiments of the present disclosure.

DESCRIPTION OF EMBODIMENTS

The following clearly describes the technical solutions in the embodiments of the present disclosure with reference to the accompanying drawings in the embodiments of the present disclosure. The described embodiments are merely some but not all of the embodiments of the present disclosure.

In the following description, specific details such as a particular system structure, an interface, and a technology are set forth in an illustrative but not a restrictive sense to make a thorough understanding of the present disclosure. However, a person skilled in the art should know that the present disclosure may be practiced in other embodiments without these specific details. In other cases, detailed descriptions of well-known mobile devices, circuits, and methods are omitted such that the present disclosure is described without being obscured by unnecessary details.

In addition, the term "and/or" in this specification describes only an association relationship for describing associated objects and represents that three relationships may exist. For example, A and/or B may represent the following three cases, only A exists, both A and B exist, and only B exists. In addition, the character "/" in this specification generally indicates an "or" relationship between the associated objects.

Ordinal numbers such as "first" and "second" mentioned in the embodiments of the present disclosure shall be understood as to serve a purpose of distinguishing only, unless they definitely express the meaning of order according to a context.

In the embodiments of the present disclosure, a method for starting an eye tracking function provided in the embodiments of the present disclosure may be executed by a mobile device or at least one processor inside a mobile device. The following specific embodiments are described by only using a mobile device as an example. The mobile device is an electronic device having an eye tracking function.

The mobile device may be a device providing voice and/or data connectivity to a user, or a handheld device having a wireless connection function, or another processing device connected to a wireless modem. The mobile device may communicate with one or more core networks using a radio access network (RAN), and may be, for example, a mobile phone (or referred to as a "cellular" phone). Further, the mobile device may be a portal device, a pocket-sized device, a handheld device, a computer built-in device, or an in-vehicle device.

Figure 1:
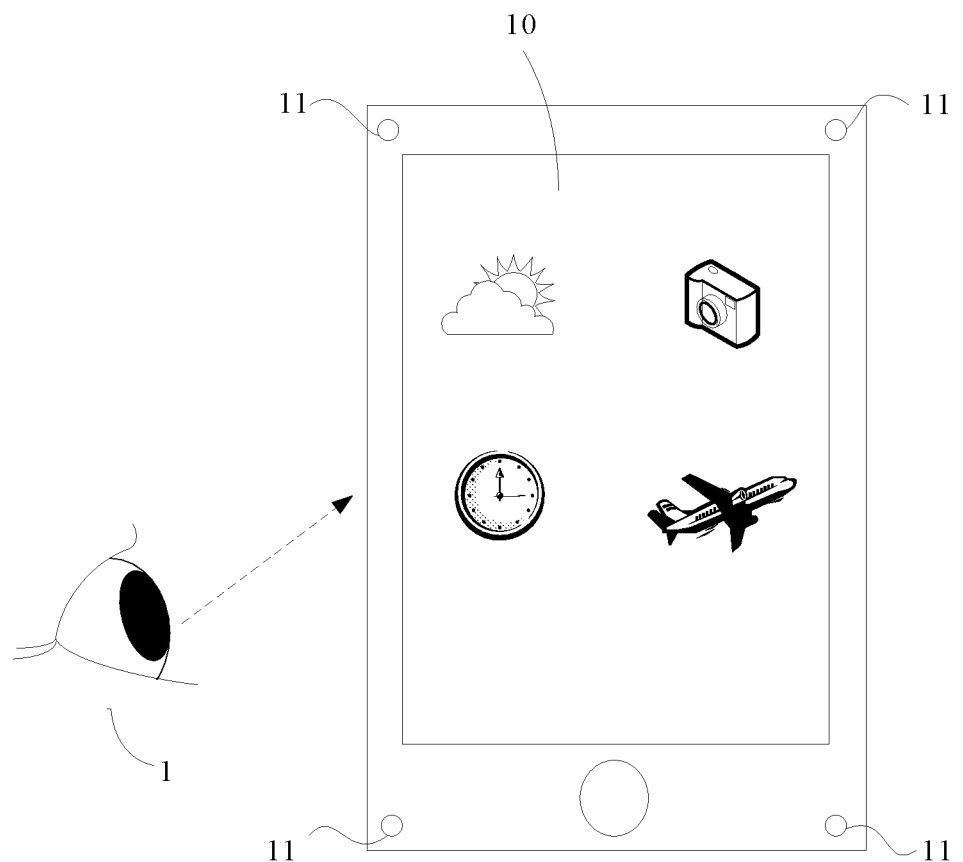
FIG. 1 is a first schematic structural diagram of a mobile device according to an embodiment of the present disclosure.

FIG. 1 is a schematic structural diagram of a mobile device having an eye tracking function according to an embodiment of the present disclosure. As shown in FIG. 1, the mobile device having an eye tracking function includes a display 10 and one or more monitors 11.

Optionally, the monitor 11 may be an infrared camera, an ordinary camera, or a device combining an infrared sensor and a camera. This is not limited in this embodiment of the present disclosure.

It can be understood that a distribution manner of the monitor 11 in the mobile device needs to depend on an actual condition.

As shown in FIG. 1, the monitor 11 is configured to monitor an eye 1 of a user and collect an action of the eye 1. An eye tracking technology is a technology that determines, mainly by collecting feature information of eye motion, a movement direction of a user's gaze and a point of the gaze. The monitor 11 may be an infrared camera, an ordinary camera, or a device combining an infrared sensor and a camera, and needs support of corresponding software to implement the eye tracking function whatever device the monitor 11 is.

Currently, relatively common eye tracking technologies may be roughly categorized into three types. A first type is that a mobile device performs tracking according to feature changes of an eye and eye surroundings. A second type is that a mobile device performs tracking according to changes of an iris. A third type is that a mobile device obtains feature information of eye motion by proactively projecting a beam, such as an infrared ray, onto an iris. It should be noted that the eye tracking technology is an existing mature technology, and details are not described herein.

Embodiment 1

Figure 2:
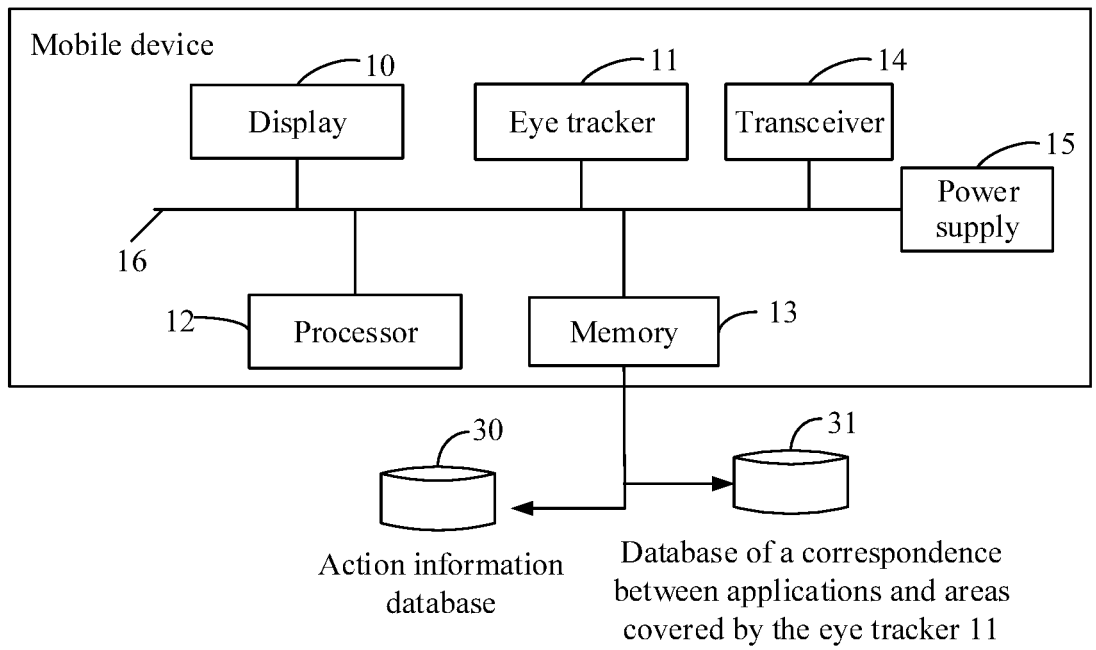
FIG. 2 is a second schematic structural diagram of a mobile device according to an embodiment of the present disclosure.

This embodiment of the present disclosure provides a mobile device, and the mobile device has an eye tracking function. As shown in FIG. 2, the mobile device includes a display 10, one or more eye tracker 11 (also referred to as monitor), a processor 12, a memory 13, a transceiver 14, and a power supply 15. The display 10, the monitor 11, the memory 13, the transceiver 14, and the power supply 15 are connected and communicate with each other using a system bus 16.

The processor 12 may be a single-core or multi-core central processing unit (CPU), or an application-specific integrated circuit (ASIC), or one or more integrated circuits configured to implement this embodiment of the present disclosure. Further, the processor 12 may be a processor having a data processing function, or may be a controller.

The memory 13 may be a high-speed random access memory (RAM), or may be a non-volatile memory, for example, at least one magnetic disk storage.

The transceiver 14 may be configured to transmit and receive information, or may be configured for signal reception and signal sending in a communication process.

The memory 13 includes an action information database 30 and a database 31 of a correspondence between applications and areas covered by the monitor. The action information database 30 is configured to provide information about various actions, for example, information about an action enabling an eye tracking mode, information about an action starting an eye tracking function, and information about an action unlocking a screen lock. The database 31 of a correspondence between applications and areas covered by the monitor stores a one-to-one correspondence between applications and areas covered by the monitor.

The processor 12 is configured to determine that the mobile device is in a preset scenario, and start at least one monitor, detect that an eye of a user has entered a monitoring area of the at least one monitor, and enable an eye tracking mode, and collect a first gaze action of the eye whose duration is not less than a first preset threshold, and start the eye tracking function, where the first gaze action is used to start the eye tracking function.

The mobile device starts the at least one monitor and monitors whether the eye tracking mode needs to be enabled, only in the preset scenario. In this way, an objective of reducing power consumption of the mobile device can be achieved.

The monitor in this embodiment of the present disclosure is any one of the at least one monitor contained by the mobile device.

Optionally, the mobile device may select any method for detecting a status of the mobile device to detect a status of the mobile device. For example, the mobile device determines a geographical location of the mobile device according to Global Positioning System (GPS) information obtained by the mobile device, or a WI-FI signal of the mobile device, or a near field communication (NFC) signal of the mobile device, or any beacon frame signal. If location information obtained by the mobile device is a meeting room, the mobile device considers by default that the user is inconvenient to operate the mobile device manually. Therefore, the mobile device starts by itself at least one monitor, and uses the at least one monitor to monitor whether the eye tracking mode needs to be enabled.

The processor 12 is further configured to obtain a straight line distance between the eye and each monitor of the mobile device, and determine a monitor at a shortest straight line distance as a to-be-started monitor.

Optionally, the monitor started by the mobile device may be any one of the at least one monitor, or may be a monitor at a shortest straight line distance from the user.

The mobile device determines the monitor at the shortest straight line distance from the eye of the user as the to-be-started monitor, and monitors, using the monitor, whether the eye of the user has entered a monitoring area of the monitor, and then determines whether the eye tracking mode needs to be enabled. In this way, a time taken to enable the eye tracking mode by the mobile device can be reduced, and the eye tracking mode can be enabled for the user within a shortest time, improving user experience.

Further, the display 10 is configured to display an interaction screen after the processor 12 starts the eye tracking function.

The interaction screen may be a screen of the mobile device or a screen of the eye tracking function. The screen of the eye tracking function includes at least one application supporting the eye tracking function.

The processor 12 is further configured to start a monitor that is not started before the display 10 displays the interaction screen.

The mobile device starts the monitor that is not started, and may set the monitor that is not started to monitor feature information of eye motion. In this way, accuracy of the feature information of eye motion obtained by the mobile device can be improved.

The processor 12 is further configured to after starting the monitor that is not started and before the display displays the interaction screen, determine whether a screen lock needs to be unlocked, determine that the screen lock needs to be unlocked, and trigger the display to display a lock screen, collect a second gaze action of the eye, determine whether the second gaze action is the same as a first preset unlock action, and unlock the screen lock if the second gaze action is the same as the first preset unlock action.

Further, after enabling the eye tracking mode, the mobile device further needs to determine whether the mobile device needs to unlock the screen lock.

In an embodiment, the user may set the eye tracking function of the mobile device to complete interaction with the mobile device, in a circumstance that the screen lock of the mobile device is not locked, or the user may set the eye tracking function of the mobile device to complete interaction with the mobile device, in a circumstance that the screen lock of the mobile device is locked.

Further, if the user uses the eye tracking function of the mobile device to complete interaction with the mobile device, in a circumstance that the screen lock of the mobile device is locked, the following two scenarios may exist.

Scenario 1: The mobile device is in a secure state, and the mobile device does not need to unlock the screen lock.

Scenario 2: The mobile device is in an insecure state, and the mobile device needs to unlock the screen lock.

Optionally, the second gaze action may be an action that the eye gazes at at least one monitor device, or may be an action that the eye gazes at a track area of at least one monitor.

Further, the second gaze action may be an action that the eye gazes at one of the at least one monitor, or may be an action combination of sequential gazes of the eye at a plurality of monitor devices of the at least one monitor.

In actual application, because a monitor device is relatively small-sized, an eye gaze of a user is not definitely accurate. Preferably, in this scenario, the mobile device may determine a gaze of the eye at a specific area near the monitor device as a gaze of the user at the monitor device.

For example, a gaze of a user at an area inside a circle whose center is a front-facing camera of a mobile phone and whose radius is one centimeter may be considered as a gaze action that the user is gazing at a monitor device.

It can be understood that track areas of a plurality of monitors of the at least one monitor may overlap. In this scenario, preferably, the mobile device includes a position at which the eye gazes into a track area of a monitor at a shortest straight line distance from the position.

For example, if the eye of the user gazes at point A of the display of the mobile device, point A belongs to both a track area of monitor 1 and a track area of monitor 2, and a straight line distance between point A and monitor 1 is shorter than that between point A and monitor 2, the mobile device considers that point A belongs to the track area of monitor 1.

The first preset unlock action may be a default action of the mobile device, or may be a user-specified action.

The processor 12 is further configured to determine whether the mobile device is in a secure state, where the secure state means that geographical location information of the mobile device is the same as preset geographical location information, or that a distance between the mobile device and a wearable device is not greater than a second preset threshold and a wireless connection has been established between the wearable device and the mobile device, and determine that the screen lock does not need to be unlocked if the mobile device is in the secure state.

The processor 12 is further configured to collect a third gaze action of the eye after the display displays the interaction screen, where the third gaze action is used to trigger start of an application on the mobile device, and start the application according to the third gaze action.

Similarly, the third gaze action in this embodiment of the present disclosure is an action that the eye gazes at at least one monitor. Optionally, the third gaze action may be an action that the eye gazes at the at least one monitor device, or may be an action that the eye gazes at a track area of the at least one monitor.

Optionally, the third gaze action may be an action that the eye gazes at one of the at least one monitor, or may be an action combination of sequential gazes of the eye at a plurality of monitor devices of the at least one monitor.

In actual application, because a monitor device is relatively small-sized, an eye gaze of a user is not definitely accurate. In this scenario, preferably, the mobile device may determine a gaze of the eye at a specific area near the monitor device as a gaze of the user at the monitor device.

For example, a gaze of a user at an area inside a circle whose center is a front-facing camera of a mobile phone and whose radius is one centimeter may be considered as a gaze action that the user is gazing at a monitor device.

Optionally, the third gaze action may be an action that the eye gazes at a track area of one of the at least one monitor, or may be an action combination of gazes of the eye at track areas of a plurality of monitors of the at least one monitor.

It should be noted that in this embodiment of the present disclosure, information about the third gaze action is not further limited.

When being an action combination of gazes of the eye at a plurality of monitor devices of the at least one monitor, or an action combination of gazes of the eye at track areas of a plurality of monitors of the at least one monitor, the third gaze action is a combination of actions completed within a specific preset time.

For example, when the user completes actions of gazing at a first sensor, a third sensor, and a second sensor continuously in sequence within five seconds, the mobile device starts a particular predetermined application.

The processor 12 is further configured to collect a close action of the eye after starting the application, where the close action is used to trigger disabling of the eye tracking mode, and disable the eye tracking mode according to the close action.

Similarly, the close action is an action that the eye gazes at the at least one monitor. Optionally, the third gaze action may be an action that the eye gazes at the at least one monitor device, or may be an action that the eye gazes at a track area of the at least one monitor.

It can be understood that the first gaze action, the second gaze action, the third gaze action, and the close action are corresponding actions when the mobile device displays different screens. Therefore, the first gaze action, the second gaze action, the third gaze action, and the close action may be the same or may be different.

The transceiver 14 is further configured to receive an instruction entered by the user, and disable the eye tracking mode according to the received instruction.

It can be understood that, when the mobile device receives an instruction entered by the user, whatever operation to complete is indicated by the instruction, it indicates that the user is no longer using the eye to interact with the mobile device at a current moment. Therefore, when receiving the instruction entered by the user, the mobile device disables the eye tracking mode according to the instruction.

Further, the preset scenario is a scenario in which the mobile device receives a notification message in a screen off state, a scenario in which the mobile device is laid flat and receives no operation, or a scenario in which the user wakes up the mobile device using voice.

The scenario in which the mobile device is laid flat and receives no operation includes a scenario in which the mobile device is in a meeting mode and a scenario in which the mobile device is in a non-meeting mode, for example, a scenario in which the mobile device is in an outdoor mode, or the mobile device is laid flat on a desk and receives no operation.

This embodiment of the present disclosure provides a mobile device. The mobile device has an eye tracking function, and the mobile device contains at least one monitor. When determining that the mobile device is in a preset scenario, the mobile device starts at least one monitor, and when detecting that an eye of a user has entered a monitoring area of the at least one monitor, the mobile device enables an eye tracking mode. After the eye tracking mode is enabled, if the mobile device collects a first gaze action of the eye whose duration is not less than a first preset threshold, the mobile device starts the eye tracking function.

According to this solution, in a condition of the preset scenario, the mobile device can enable the eye tracking mode when detecting, using the monitor, that the eye of the user has entered the monitoring area of the at least one monitor. Further, after the eye tracking mode is enabled, if the mobile device collects, using the at least one monitor, the first gaze action of the eye whose duration is not less than the first preset threshold, the mobile device starts the eye tracking function. This avoids a problem of poor convenience that, in the condition of the preset scenario, a user cannot use, before the user starts an eye tracking function manually, the eye tracking function of a mobile device to complete a related service. The present disclosure implements that the mobile device starts by itself the eye tracking function, making it more convenient for the user to use the mobile device.

Embodiment 2

Figure 3:
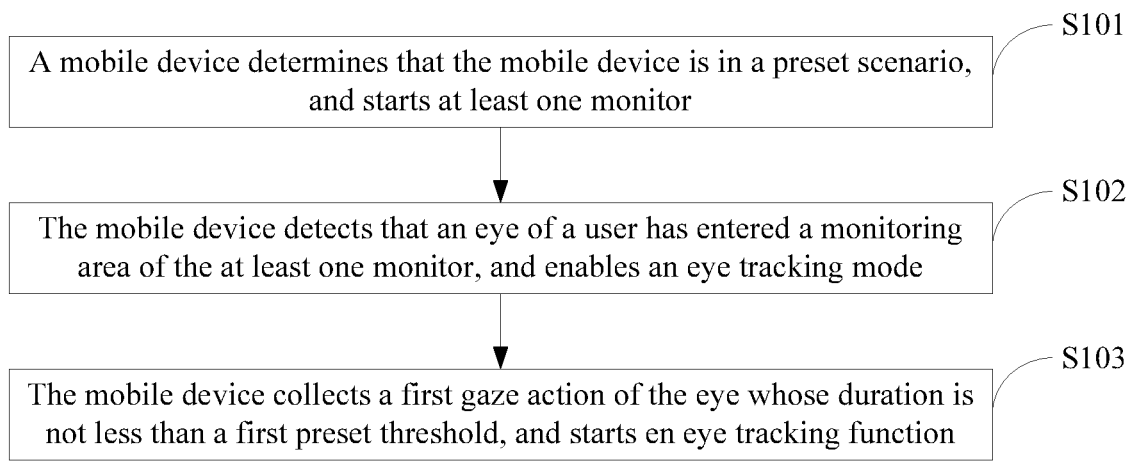
FIG. 3 is a first schematic flowchart of a method for starting an eye tracking function according to an embodiment of the present disclosure.

This embodiment of the present disclosure provides a method for starting an eye tracking function. The method is applied to a mobile device having an eye tracking function, and as shown in FIG. 3, includes the following steps.

Step S101: The mobile device determines that the mobile device is in a preset scenario, and starts at least one monitor.

Step S102: The mobile device detects that an eye of a user has entered a monitoring area of the at least one monitor, and enables an eye tracking mode.

Step S103: The mobile device collects a first gaze action of the eye whose duration is not less than a first preset threshold, and starts the eye tracking function.

The first gaze action is used to start the eye tracking function.

The preset scenario in this embodiment of the present disclosure is a scenario in which the mobile device receives a notification message in a screen off state, a scenario in which the mobile device is laid flat and receives no operation, or a scenario in which the user wakes up the mobile device using voice.

The scenario in which the mobile device is laid flat and receives no operation includes a scenario in which the mobile device is in a meeting mode and a scenario in which the mobile device is in a non-meeting mode, for example, a scenario in which the mobile device is in an outdoor mode, or the mobile device is laid flat on a desk and receives no operation.

It should be noted that the preset scenario in this embodiment of the present disclosure is not limited to the foregoing several scenarios, and may alternatively be another scenario in which the user is inconvenient to operate the mobile device manually. This is not limited in this embodiment of the present disclosure.

In the preset scenario, the mobile device starts the at least one monitor and uses the at least one monitor to monitor whether the eye tracking mode needs to be enabled. In this way, an objective of reducing power consumption of the mobile device can be achieved.

The monitor started by the mobile device in this embodiment of the present disclosure may be any one of the at least one monitor contained by the mobile device.

Further, before the mobile device starts the at least one monitor, and sets the at least one monitor to monitor whether the eye tracking mode needs to be enabled, the mobile device detects whether the mobile device is in the preset scenario. That is, the mobile device first determines a status of the mobile device, and if the mobile device is in the preset scenario, the mobile device starts the at least one monitor, and sets the at least one monitor to monitor whether the eye tracking mode needs to be enabled.

It should be noted that a method for detecting the status of the mobile device by the mobile device is any method for detecting the status of the mobile device. The method for detecting the status of the mobile device is an existing mature technology, and details are not described herein.

For example, if the mobile device obtains by means of detection that location information of the mobile device is a meeting room (for example, GPS information of the mobile device is a meeting room, WI-FI signal area information of the mobile device is a meeting room, or NFC information of the mobile device is a meeting room), in this case, the mobile device considers by default that the user is inconvenient to perform a manual operation. Therefore, the mobile device starts the at least one monitor, and uses the started at least one monitor to monitor whether the eye tracking mode needs to be enabled.

If the mobile device determines, using an acceleration sensor of the mobile device or a gyro sensor of the mobile device, that the mobile device is still or laid flat, and the mobile device determines, using a proximity sensor of the mobile device, that the mobile device is not in contact with the user, the mobile device starts the at least one monitor, and sets the started at least one monitor to monitor whether the eye tracking mode needs to be enabled.

The proximity sensor is a general term for sensors serving a purpose of performing detection without touching a detected object. The proximity sensor can convert movement information and presence information of the detected object into an electrical signal. The proximity sensor may convert the motion information and presence information of the detected object into the electrical signal by means of setting electromagnetic induction to cause generation of an eddy current in a metal body of the detected object, capturing a capacity change of the electrical signal of the detected object caused by proximity of a detection body, or an inductive switch.

Further, if the monitor of the mobile device detects that the eye of the user has entered the monitoring area of the started at least one monitor, the mobile device enables the eye tracking mode.

It can be understood that, that the eye has entered the monitoring area of the at least one monitor indicates that a relative distance between the user and the mobile device is relatively small, and that the mobile device considers by default that the eye has entered the monitoring area of the at least one monitor represents that the user hopes to enable the eye tracking mode.

In this embodiment of the present disclosure, the mobile device can enable the eye tracking mode when the eye of the user has entered a monitoring area of one of the started at least one monitor.

Optionally, at the same time when enabling the eye tracking mode, the mobile device may trigger lighting up a display, or may keep a display unchanged. This is not further limited in this embodiment of the present disclosure.

Figure 4:
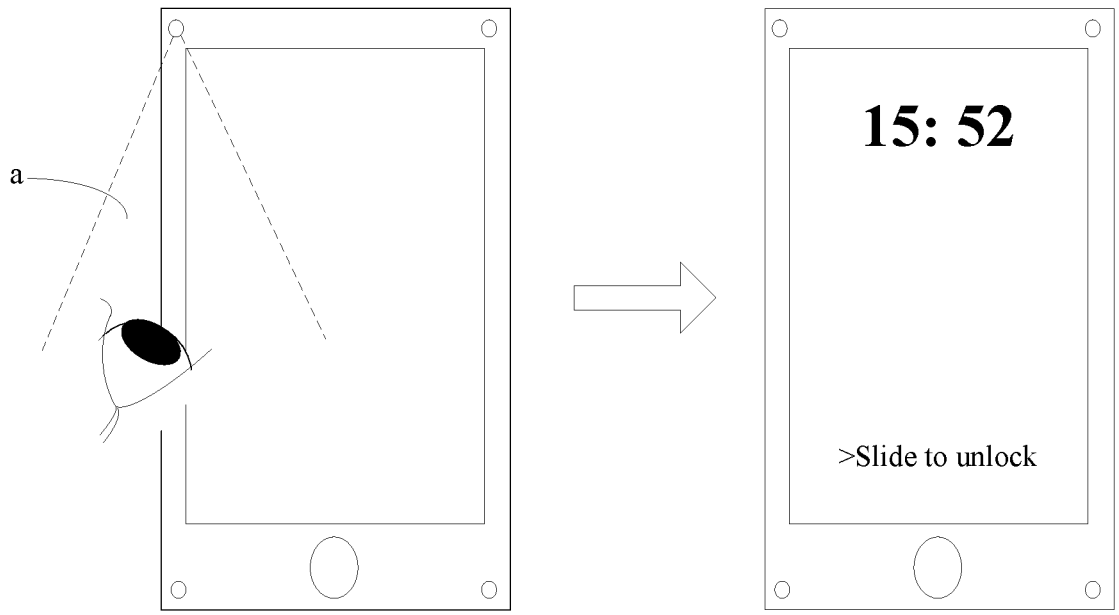
FIG. 4 is a schematic diagram of enabling an eye tracking mode according to an embodiment of the present disclosure.

For example, as shown in FIG. 4, using the mobile device shown in FIG. 1 as an example, it is assumed that a monitor on the top left is a monitor started when the mobile device is in a preset scenario, and that area a is a first area. When the mobile device is in a meeting mode, after the mobile device identifies a status of the mobile device, the mobile device starts the monitor on the top left, and sets the monitor on the top left to monitor whether the eye tracking mode needs to be enabled. When the eye of the user has entered area a, the mobile device enables the eye tracking mode and triggers lighting up the display. Area a may be a sector coverage area whose vertex is the monitor on the top left and whose angle is less than 180 degrees.

Optionally, a method for detecting, by the mobile device, that the eye has entered the monitoring area of the monitor may be as follows. The mobile device first uses the at least one monitor to detect that a face of the user has entered the monitoring area of the at least one monitor, and then, the mobile device obtains the eye from a face image.

A method for obtaining the eye from the face image by the mobile device is an existing mature technology, and is not further limited in this embodiment of the present disclosure.

Further, the mobile device may determine, using a software algorithm, whether the face image collected by the mobile device includes the eye.

Further, the mobile device radiates near-infrared light to the eye by alternately projecting light sources in different directions, to obtain eye information.

For example, when infrared light source projection is near an optical axis of a camera, and light emitted from the infrared light source is approximately parallel to the optical axis of the camera, most light reaching a pupil from the infrared light source is reflected back to the camera, and a phenomenon of "bright pupil" appears in the image. Conversely, when light emitted from an infrared light source is far away from the optical axis of the camera, and an angle between the light emitted from the infrared light source and the optical axis of the camera is relatively large, little light reaching the pupil from the infrared light source is reflected back to the camera, and a "dark pupil" appears. The mobile device performs filtering on a collected bright pupil image and a collected dark pupil image (performs filtering on two adjacent frames of the bright pupil image and the dark pupil image) to obtain a position of the pupil. The mobile device filters face contours and displays the position of the pupil in a resulting image, analyzes a shape, a size, and a grayscale value of the pupil in a connected region of the image, and determines a corresponding threshold and a determining condition, and cancels face interference to obtain a final image of the eye.

Then, the mobile device positions a pupil center and a Purkinje spot. The mobile device finds a position of the pupil using a global search method, and a Purkinje spot has a relatively high grayscale value in the pupil. After the pupil is positioned, the mobile device determines a position of the Purkinje spot according to the dark pupil image and a grayscale. The mobile device calculates, according to information about a vector between the pupil center and a center of the Purkinje spot, a specific position at which the eye gazes.

Optionally, a method for detecting, by the mobile device, that the eye has entered the monitoring area of the at least one monitor may be that the mobile device directly uses the at least one monitor to detect that the eye of the user has entered the monitoring area of the at least one monitor.

Further, after the mobile device enables the eye tracking mode, the mobile device sets the at least one monitor to monitor whether the eye tracking function needs to be started.

Further, if the at least one monitor collects, in the monitoring area of the at least one monitor, a first gaze action of the eye whose duration is not less than the first preset threshold, the mobile device starts the eye tracking function. The first gaze action is used to trigger start of the eye tracking function.

The eye tracking function in this embodiment of the present disclosure is that the mobile device collects feature information of eye motion and can implement a corresponding response according to the feature information of eye motion. After enabling the eye tracking mode, the mobile device may not start the eye tracking function. In this way, power consumption of the mobile device can be reduced in some scenarios.

The first gaze action is an action that the eye of the user gazes at a monitoring area of the monitor. In this embodiment of the present disclosure, specific action information of the first gaze action is not limited.

This embodiment of the present disclosure provides a method for starting an eye tracking function, and the method is applied to a mobile device having an eye tracking function. When the mobile device is in a preset scenario, the mobile device starts at least one monitor, and when detecting that an eye of a user has entered a monitoring area of the at least one monitor, the mobile device enables an eye tracking mode. After the eye tracking mode is enabled, if the mobile device collects a first gaze action of the eye whose duration is not less than a first preset threshold, the mobile device starts the eye tracking function.

According to this solution, in a condition of the preset scenario, the mobile device can enable the eye tracking mode when detecting, using the at least one monitor, that the eye of the user has entered the monitoring area of the at least one monitor. Further, after the eye tracking mode is enabled, if the mobile device collects, using the at least one monitor, the first gaze action of the eye whose duration is not less than the first preset threshold, the mobile device starts the eye tracking function. This avoids a problem of poor convenience that, in the condition of the preset scenario, a user cannot use, before the user starts an eye tracking function manually, the eye tracking function of a mobile device to complete a related service. The present disclosure implements that the mobile device starts by itself the eye tracking function, making it more convenient for the user to use the mobile device.

Embodiment 3

This embodiment of the present disclosure provides a method for starting an eye tracking function. In a preset scenario, a mobile device having an eye tracking function starts at least one monitor, monitors motion of an eye using the at least one monitor, and correspondingly enables an eye tracking mode and the eye tracking function. This enables the mobile device to start the eye tracking function by itself, and makes it more convenient for a user to use the mobile device.

This embodiment of the present disclosure is described using an example in which the mobile device starts a first monitor in the preset scenario.

Figure 5:
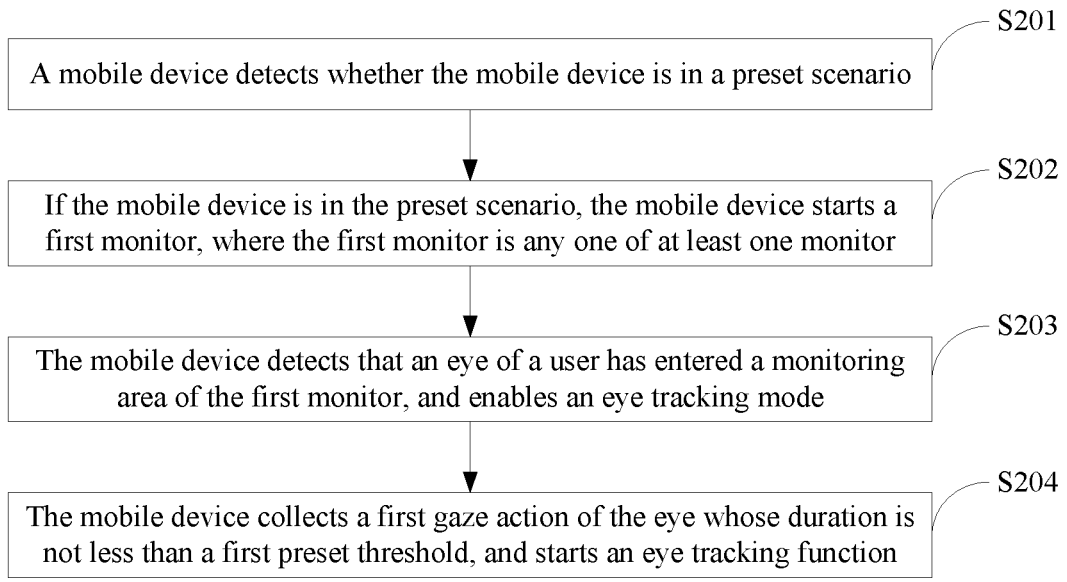
FIG. 5 is a second schematic flowchart of a method for starting an eye tracking function according to an embodiment of the present disclosure.

The method described in this embodiment of the present disclosure is applicable to the following two different application scenarios. As shown in FIG. 5, the first monitor is any one of the at least one monitor, as shown in FIG. 6, the first monitor is a monitor at a shortest straight line distance from the eye of the user.

Figure 6:
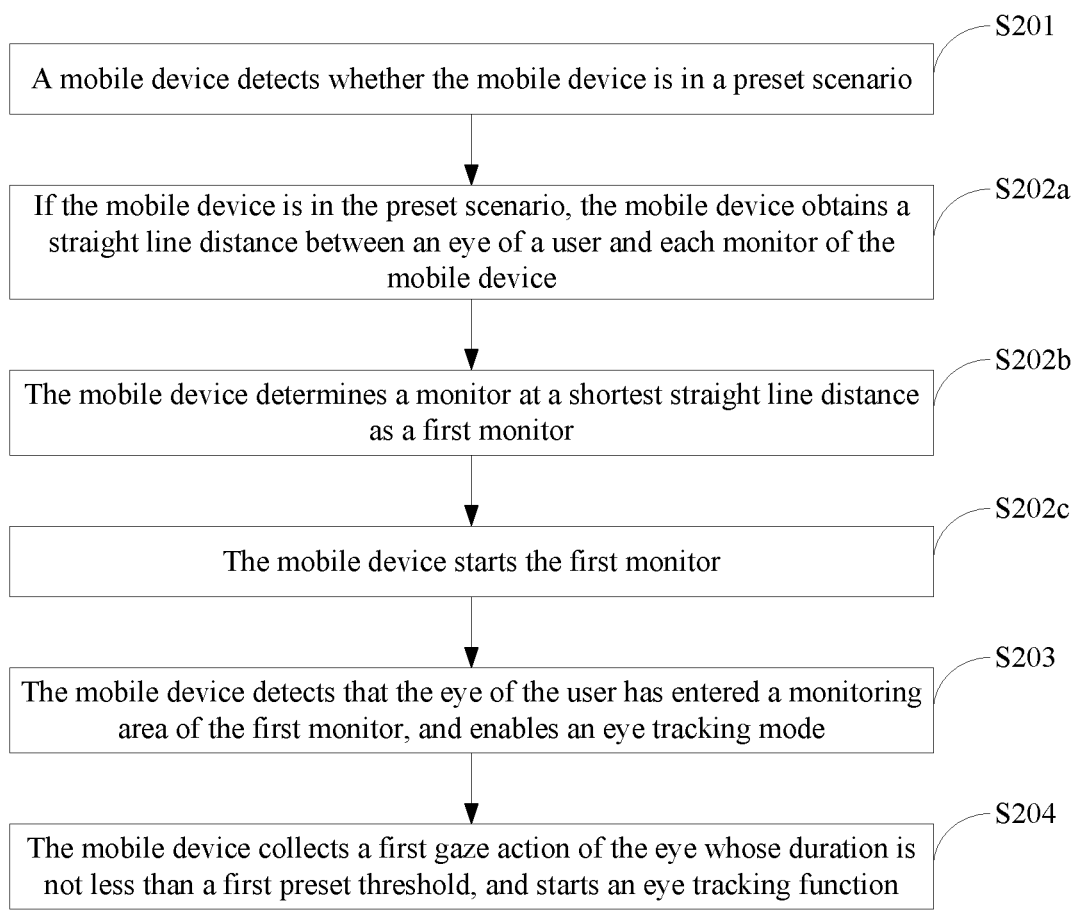
FIG. 6 is a third schematic flowchart of a method for starting an eye tracking function according to an embodiment of the present disclosure.

As shown in FIG. 5 or FIG. 6, the method for starting an eye tracking function provided in this embodiment of the present disclosure includes the following steps.

Step S201: A mobile device detects whether the mobile device is in a preset scenario.

The preset scenario is a scenario in which the mobile device receives a notification message in a screen off state, a scenario in which the mobile device is laid flat and receives no operation, or a scenario in which a user wakes up the mobile device using voice.

The scenario in which the mobile device is laid flat and receives no operation includes a scenario in which the mobile device is in a meeting mode and a scenario in which the mobile device is in a non-meeting mode, for example, a scenario in which the mobile device is in an outdoor mode, or the mobile device is laid flat on a desk and receives no operation.

It should be noted that the preset scenario in this embodiment of the present disclosure is not limited to the foregoing several scenarios, and may alternatively be another scenario in which the user is inconvenient to operate the mobile device manually. This is not limited in this embodiment of the present disclosure.

Further, the mobile device may detect, using any method for detecting a status of the mobile device, whether the mobile device is in the preset scenario.

The method for detecting the status of the mobile device is an existing mature technology, and details are not described herein.

Step S202: If the mobile device is in the preset scenario, the mobile device starts a first monitor, where the first monitor is any one of at least one monitor.

Further, in a second application scenario of this embodiment of the present disclosure, the first monitor is a monitor at a shortest straight line distance from an eye of the user.

Further, in the second application scenario, as shown in FIG. 6, step S202 in a first application scenario of this embodiment of the present disclosure may be replaced with steps S202*a*, S202*b*, and S202*c*.

Step S202*a*: If the mobile device is in the preset scenario, the mobile device obtains a straight line distance between an eye of a user and each monitor of the mobile device.

The mobile device obtains the straight line distance between the eye of the user and each monitor of the mobile device. The mobile device may use a voice recognition technology, a voiceprint recognition technology, collection of the user's breath using a microphone, ultrasound measurement, infrared sensor measurement, proximity sensor measurement, or optical sensor measurement to obtain the straight line distance between the eye of the user and each monitor.

Step S202*b*: The mobile device determines a monitor at a shortest straight line distance as a first monitor.

Step S202*c*: The mobile device starts the first monitor.

After obtaining the straight line distance between the eye of the user and each monitor, the mobile device determines the monitor at the shortest straight line distance as the first monitor, and then, the mobile device starts the first monitor. Further, the mobile device uses the first monitor to monitor whether an eye tracking mode needs to be enabled.

The mobile device determines the monitor at the shortest straight line distance from the user as a first eye tracker, and sets the first monitor to monitor whether the eye of the user has entered a first area, and then determines whether the eye tracking mode needs to be enabled. In this way, a time taken to enable the eye tracking mode by the mobile device can be reduced, and the eye tracking mode can be enabled for the user within a shortest time, improving user experience.

Further, as shown in FIG. 5 or FIG. 6, in both cases in which the first monitor is any one of the at least one monitor and the first monitor is the monitor at the shortest straight line distance from the user, the mobile device uses the first monitor to monitor whether the eye tracking mode needs to be enabled.

Step S203: The mobile device detects that an eye of the user has entered a monitoring area of the first monitor, and enables an eye tracking mode.

Step S204: The mobile device collects a first gaze action of the eye whose duration is not less than a first preset threshold, and starts an eye tracking function.

The first gaze action is used to trigger start of the eye tracking function.

Step S203 in this embodiment of the present disclosure is the same as step S102 in Embodiment 1, and step S204 is the same as step S103 in Embodiment 1. Details are not described herein any further.

The mobile device having the eye tracking function starts the first monitor in the preset scenario, and the mobile device can enable the eye tracking mode when detecting, using the first monitor, that the eye has entered a coverage area of the first monitor.

Further, after the eye tracking mode is enabled, if the mobile device collects, using the first monitor, the first gaze action of the eye in the first area whose duration is greater than or equal to the first preset threshold, the mobile device starts the eye tracking function. This avoids a problem of poor convenience that, in the condition of the preset scenario, a user cannot use, before the user starts an eye tracking function manually, the eye tracking function of a mobile device to complete a related service. The present disclosure implements that the mobile device starts by itself the eye tracking function, making it more convenient for the user to use the mobile device.

Further, after the mobile device starts the eye tracking function, the mobile device determines whether another monitor different from the first monitor is started, and performs corresponding processing according to a determining result. Then, the mobile device determines whether unlocking is needed, and performs corresponding processing according to a determining result such that the user interacts with the mobile device with the eye.

Figure 7:
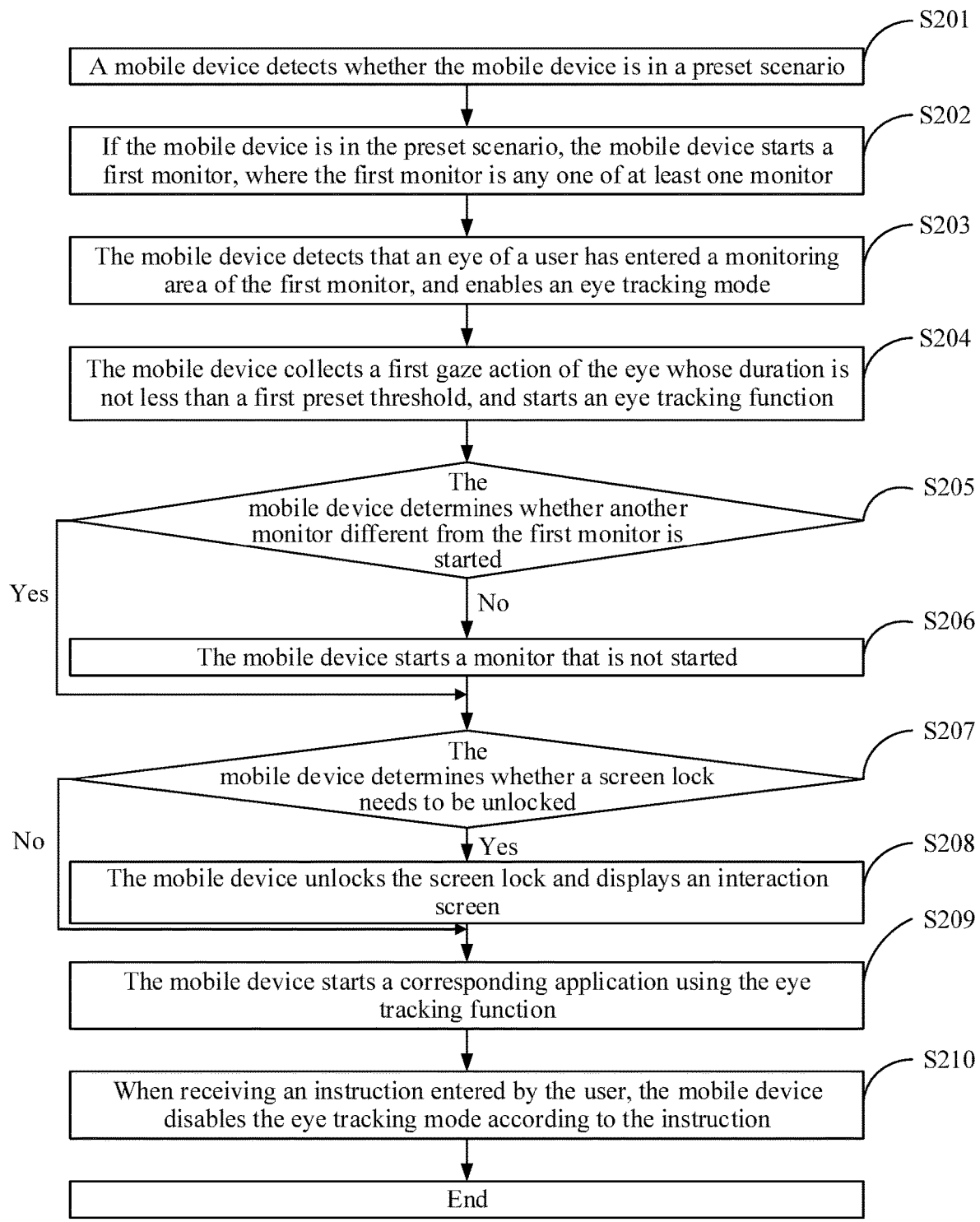
FIG. 7 is a fourth schematic flowchart of a method for starting an eye tracking function according to an embodiment of the present disclosure.
Figure 8:
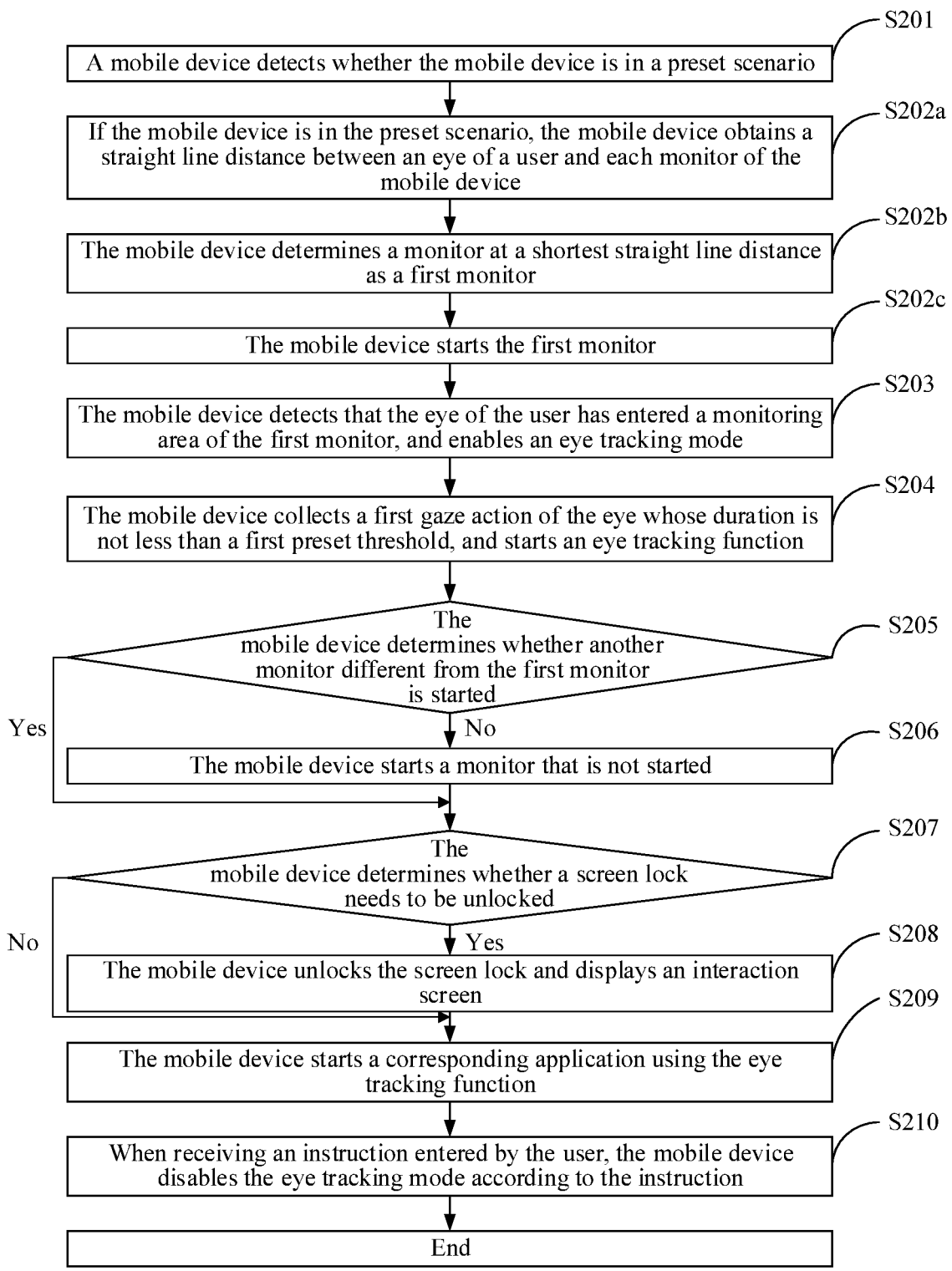
FIG. 8 is a fifth schematic flowchart of a method for starting an eye tracking function according to an embodiment of the present disclosure.

Further, as shown in FIG. 7 or FIG. 8, after step S204, the method for starting an eye tracking function provided in this embodiment of the present disclosure further includes the following steps.

Step S205: The mobile device determines whether another monitor different from the first monitor is started.

Step S206: If there is another monitor not started, the mobile device starts the monitor that is not started.

After starting the eye tracking function, the mobile device determines whether another monitor different from the first monitor is started. If there is another monitor not started, the mobile device starts the monitor that is not started. In this way, the mobile device can collect, using the at least one monitor, feature information of eye motion, and therefore, accuracy of the feature information of eye motion obtained by the mobile device can be improved.

Step S207: The mobile device determines whether a screen lock needs to be unlocked.

In an embodiment, the user may set the eye tracking function of the mobile device to complete interaction with the mobile device, in a circumstance that the screen lock of the mobile device is not locked, or the user may use the eye tracking function of the mobile device to complete interaction with the mobile device, in a circumstance that the screen lock of the mobile device is locked.

Further, the mobile device first determines whether a display of the mobile device is locked. If the display is locked, the mobile device determines whether the screen lock needs to be unlocked. If the display is unlocked, the mobile device does not need to unlock the screen lock.

Further, if the display is locked, a method for determining, by the mobile device, whether the screen lock needs to be unlocked may be determining whether the mobile device is in a secure state by the mobile device.

If the mobile device is in the secure state, the mobile device does not need to unlock the screen lock, and may directly display an interaction screen such that the mobile device can start a corresponding application using the eye tracking function.

The interaction screen may be a home page of the mobile device or a screen of the eye tracking function. The screen of the eye tracking function includes at least one application supporting the eye tracking function.

Further, if the mobile device does not need to unlock the screen lock, after performing step S207, the mobile device performs step S209.

The secure state means that geographical location information of the mobile device is the same as preset geographical location information, or that a distance between the mobile device and a wearable device is not greater than a second preset threshold and a wireless connection has been established between the wearable device and the mobile device.

Step S208: If the screen lock needs to be unlocked, the mobile device unlocks the screen lock and displays an interaction screen.

Further, if the mobile device determines that the mobile device needs to unlock the screen lock, the mobile device displays a lock screen, and unlocks the screen lock using any screen lock unlocking manner in other approaches. Alternatively, the mobile device may collect a second gaze action of the eye, and determine whether the second gaze action is the same as a first preset unlock action, and if the second gaze action is the same as the first preset unlock action, the mobile device unlocks the screen lock.

For example, the mobile device may unlock the screen lock using a face recognition technology, or may unlock the screen lock using a voice control technology.

Step S209: The mobile device starts a corresponding application using the eye tracking function.

Step S210: When receiving an instruction entered by the user, the mobile device disables the eye tracking mode according to the instruction.

The application is a computer program that is developed to complete one or more specific tasks and that runs on an operating system. The application in this embodiment of the present disclosure is an application compatible with a system loaded on the mobile device.

It should be noted that the system loaded on the mobile device may be an ANDROID operating system, or may be another system such as an IOS. This is not limited in this embodiment of the present disclosure. As the system loaded on the mobile device may be an Android operating system or another system, a format of the application varies with the system.

For example, if the system loaded on the mobile device is an ANDROID operating system, a format of the application is application package file (APK).

The APK is an application installation file format on an ANDROID operating system. To run on an ANDROID device, code of an ANDROID application needs to be compiled first, and then packed into a file recognizable by the ANDROID system. This file format that can be recognized and run by the ANDROID system is APK. An APK file includes a compiled code file (a .dex file), file resources, assets, certificates, and a manifest file.

Optionally, a method for starting the corresponding application by the mobile device using the eye tracking function may be starting the corresponding application by the mobile device using an eye tracking function technology in the other approaches, or may be that the mobile device collects a third gaze action of the eye using the at least one monitor and rapidly starts the application according to the third gaze action. The third gaze action is used to trigger start of the application on the mobile device, and the application is any application on the mobile device.

Further, when receiving the instruction entered by the user, the mobile device disables the eye tracking mode according to the instruction.

It can be understood that, when the mobile device receives an instruction entered by the user, whatever operation to complete is indicated by the instruction, it indicates that the user is no longer using the eye to interact with the mobile device at a current moment. Therefore, when receiving the instruction entered by the user, the mobile device disables the eye tracking mode according to the instruction.

Optionally, the instruction entered by the user may be an instruction to disable the eye tracking mode, or may be an instruction to return to an operation. This is not limited in this embodiment of the present disclosure.

Further, when unlocking the screen lock, the mobile device unlocks the screen lock using an eye tracking technology.

Figure 9:
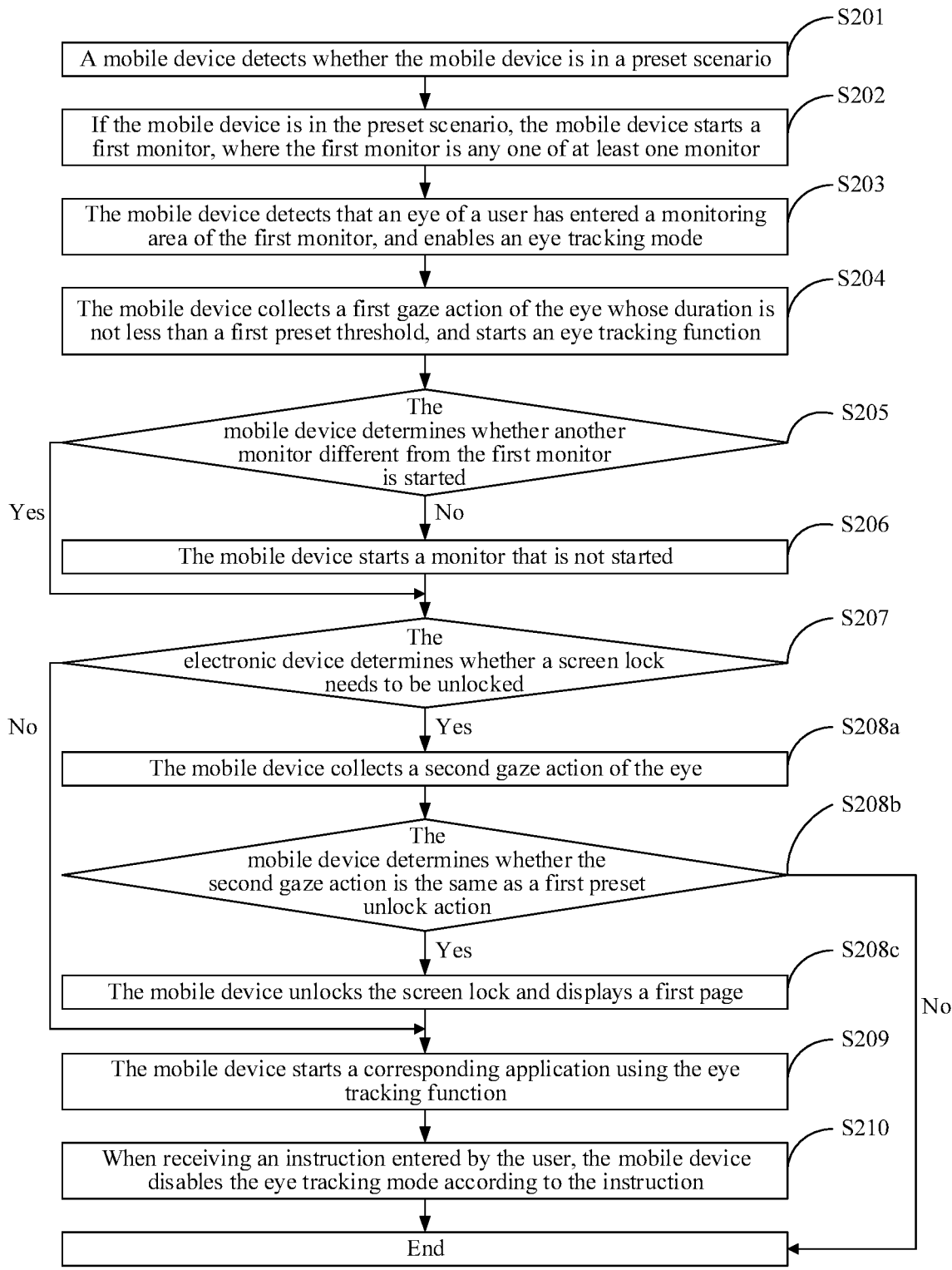
FIG. 9 is a sixth schematic flowchart of a method for starting an eye tracking function according to an embodiment of the present disclosure.
Figure 10A:
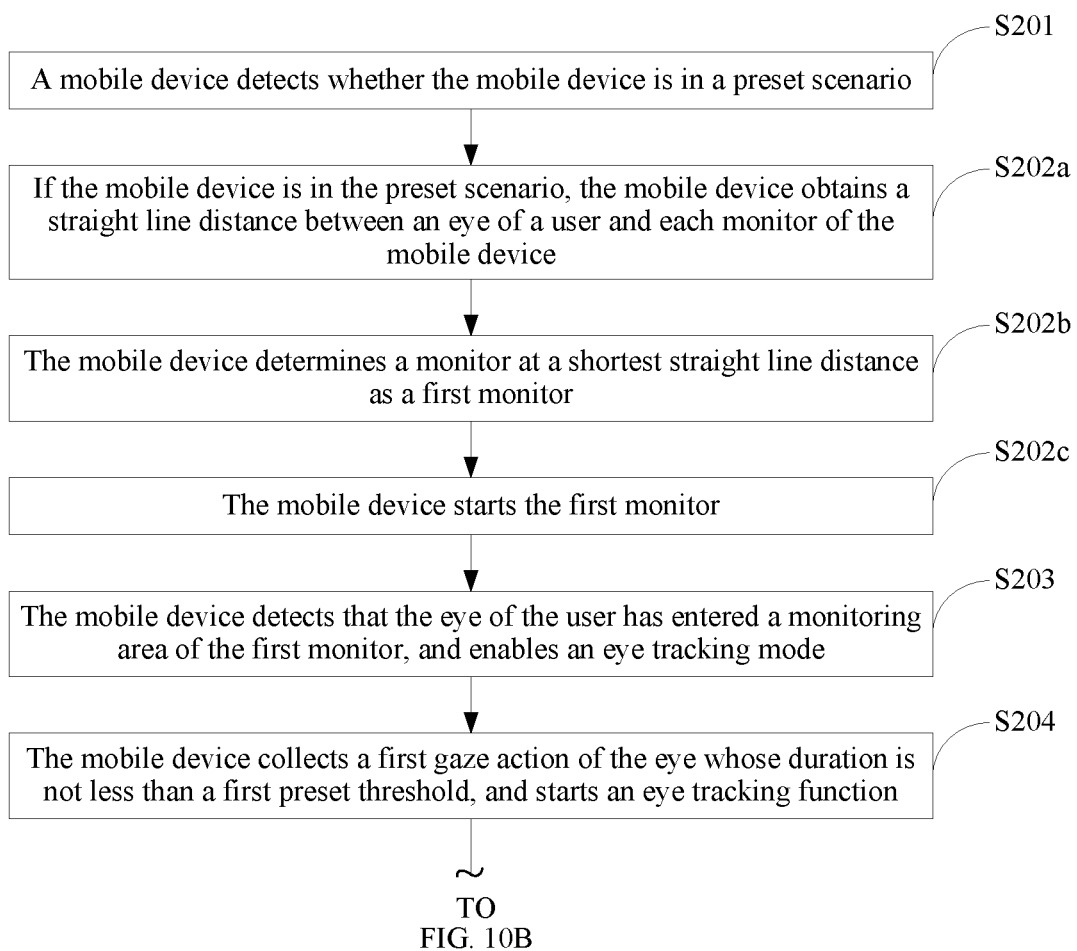
FIG. 10A and FIG. 10B are a seventh schematic flowchart of a method for starting an eye tracking function according to an embodiment of the present disclosure.
Figure 10B:
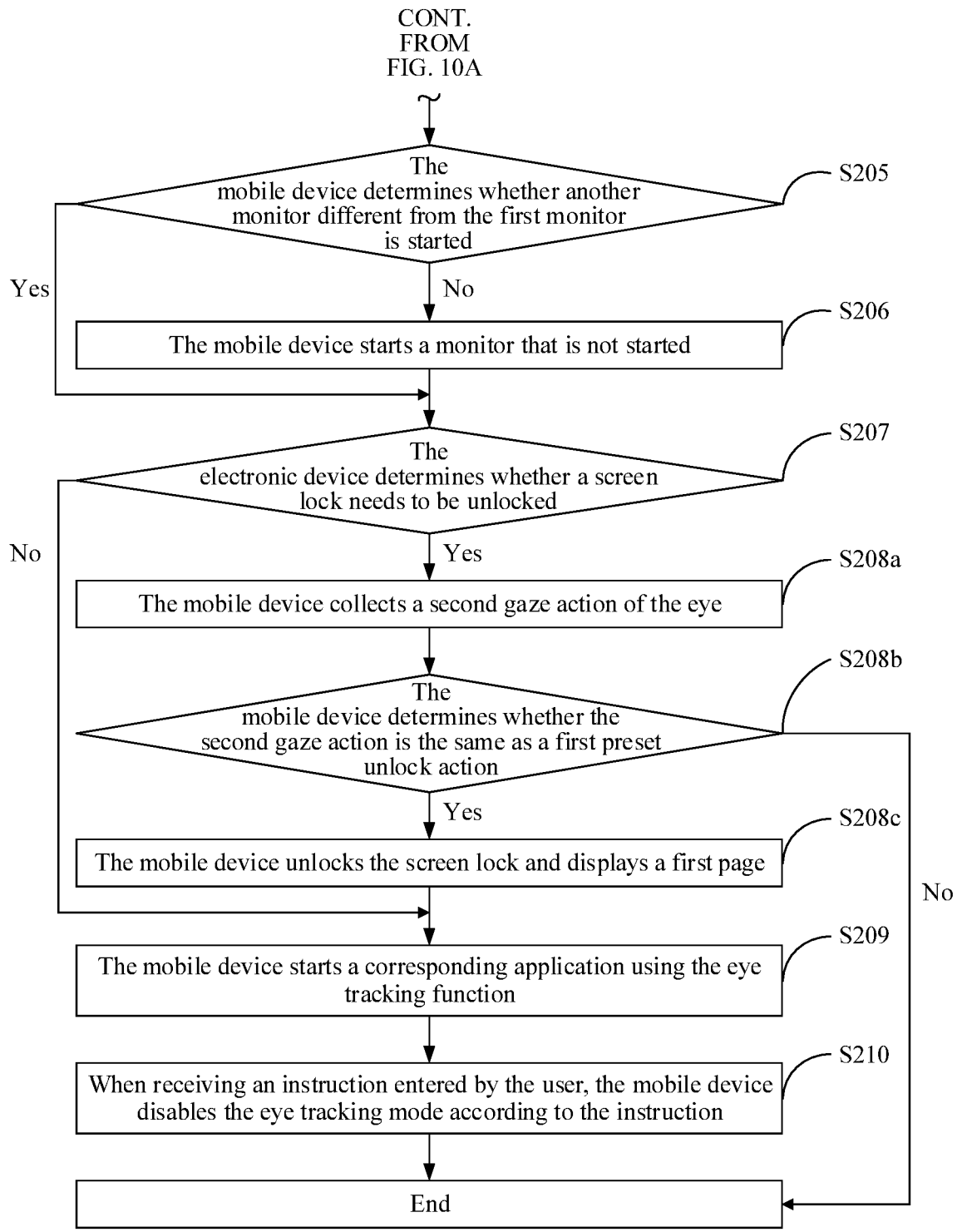

Further, as shown in FIG. 9 or FIG. 10B, step S208 may be replaced with steps S208a, S208b, and S208c.

Step S208a: If the screen lock needs to be unlocked, the mobile device collects a second gaze action of the eye.

The second gaze action is an action that the eye gazes at the at least one monitor.

Optionally, the second gaze action may be an action that the eye gazes at the at least one monitor device, or may be an action that the eye gazes at a track area of the at least one monitor.

Further, the second gaze action may be an action that the eye gazes at one of the at least one monitor, or may be an action combination of sequential gazes of the eye at a plurality of monitor devices of the at least one monitor.

Further, the second gaze action may be an action that the eye gazes at a track area of one of the at least one monitor, or may be an action combination of gazes of the eye at track areas of a plurality of monitors of the at least one monitor.

In an embodiment, because a monitor device is relatively small-sized, an eye gaze of a user is not definitely accurate. In this scenario, preferably, the mobile device may determine a gaze of the eye at a specific area near the monitor device as a gaze of the user at the monitor device.

For example, a gaze of a user at an area inside a circle whose center is a front-facing camera of a mobile phone and whose radius is one centimeter may be considered as a gaze action that the user is gazing at a monitor device.

It is easy to understood that track areas of a plurality of monitors of the at least one monitor may overlap. In this scenario, preferably, the mobile device includes a position at which the eye gazes into a track area of a monitor at a shortest straight line distance from the position.

For example, the second gaze action is sequential gazes of the eye at the first area, a second area, and a fourth area.

Step S208b: The mobile device determines whether the second gaze action is the same as a first preset unlock action.

Optionally, the first preset unlock action may be a default action of the mobile device, or may be a user-specified action.

It should be noted that in this embodiment of the present disclosure, information about the first preset unlock action is not limited.

For example, the first preset unlock action is a gaze of the eye at the first area, and a wink frequency of two eyes within a preset time is equal to a third preset threshold.

Further, if the second gaze action is the same as the first preset unlock action, the mobile device unlocks the screen lock and displays an interaction screen. If the second gaze action is different from the first preset unlock action, the mobile device does not perform an operation of unlocking the screen lock.

Figure 11:
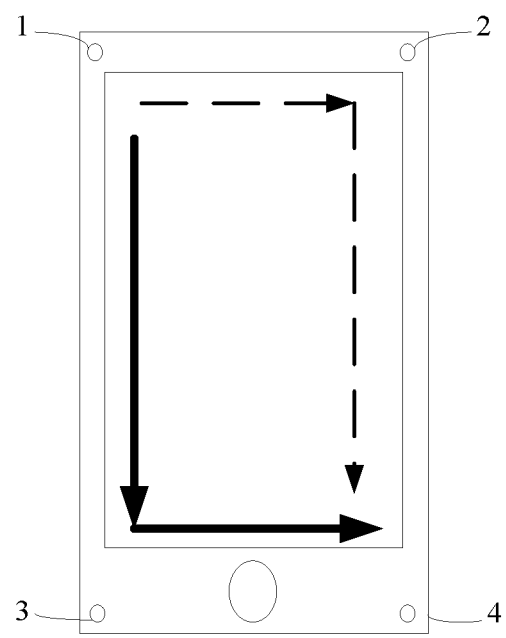
FIG. 11 is a schematic diagram of unlocking a screen lock according to an embodiment of the present disclosure.

For example, as shown in FIG. 11, using the mobile device shown in FIG. 1 as an example, if four monitors in the mobile device are sequentially monitor 1, monitor 2, monitor 3, and monitor 4 in clockwise order, and track areas of monitor 1, monitor 2, monitor 3, and monitor 4 are sequentially area 1, area 2, area 3, and area 4. A second preset unlock action is sequential gazes of the eye at area 1, area 2, and area 4, that is, presenting a shape shown by dotted lines in the figure.

If a third gaze action of the eye collected by the mobile device using monitor 1, monitor 2, monitor 3, and monitor 4 is sequential gazes of the eye at area 1, area 3, and area 4, that is, presenting a shape shown by solid lines in the figure, because the shape shown by the dotted lines is different from the shape shown by the solid lines, the mobile device does not perform the operation of unlocking the screen lock.

Step S208c: If the second gaze action is the same as the first preset unlock action, the mobile device unlocks the screen lock and displays an interaction screen.

The interaction screen may be a home page of the mobile device or a screen of the eye tracking function. The screen of the eye tracking function includes at least one application supporting the eye tracking function.

That is, if the second gaze action is the same as the first preset unlock action, the mobile device unlocks the screen lock and directly displays the home page of the mobile device or the screen of the eye tracking function.

Further, in the other approaches, after a mobile device starts an eye tracking function, when a user uses an eye to interact with the mobile device, the user usually needs to gaze at the mobile device for a long time, and before an eye tracking cursor is displayed on a display of the mobile device, the user cannot use the eye to select an object on the display of the mobile device to allow a further operation on the selected object. This process is relatively cumbersome, and the user needs to use the eye to search level by level. The entire process is time-consuming and labor-consuming.

To enable the user to use an eye to rapidly operate the mobile device, in the method for starting an eye tracking function provided in this embodiment of the present disclosure, the mobile device quickly starts, by collecting a third gaze action of the eye, an application corresponding to the third gaze action.

Figure 12A:
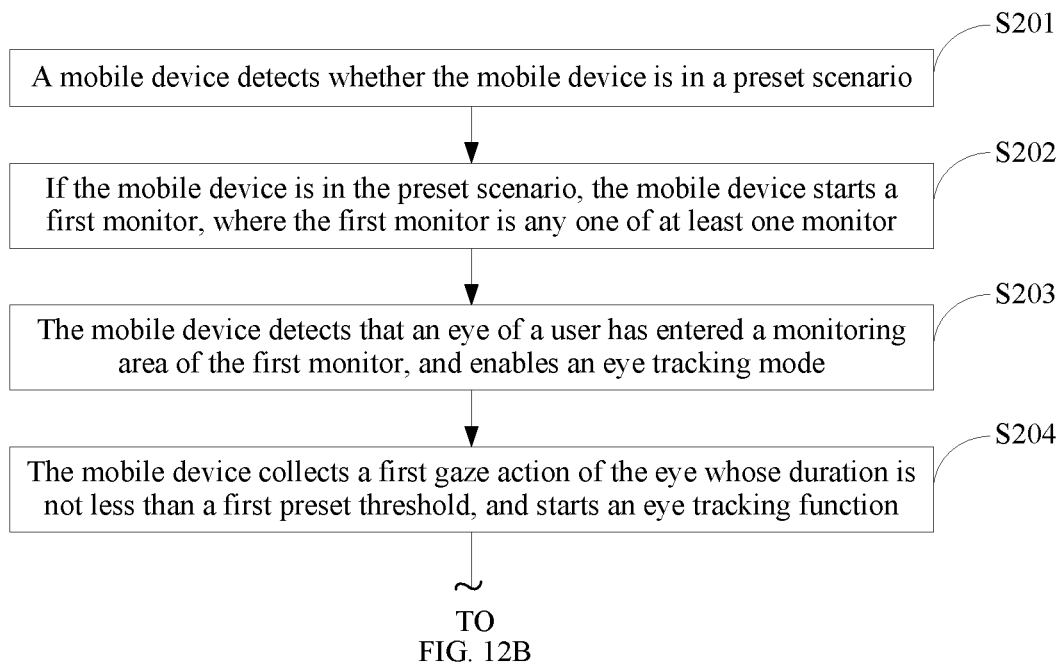
FIG. 12A and FIG. 12B are an eighth schematic flowchart of a method for starting an eye tracking function according to an embodiment of the present disclosure.
Figure 12B:
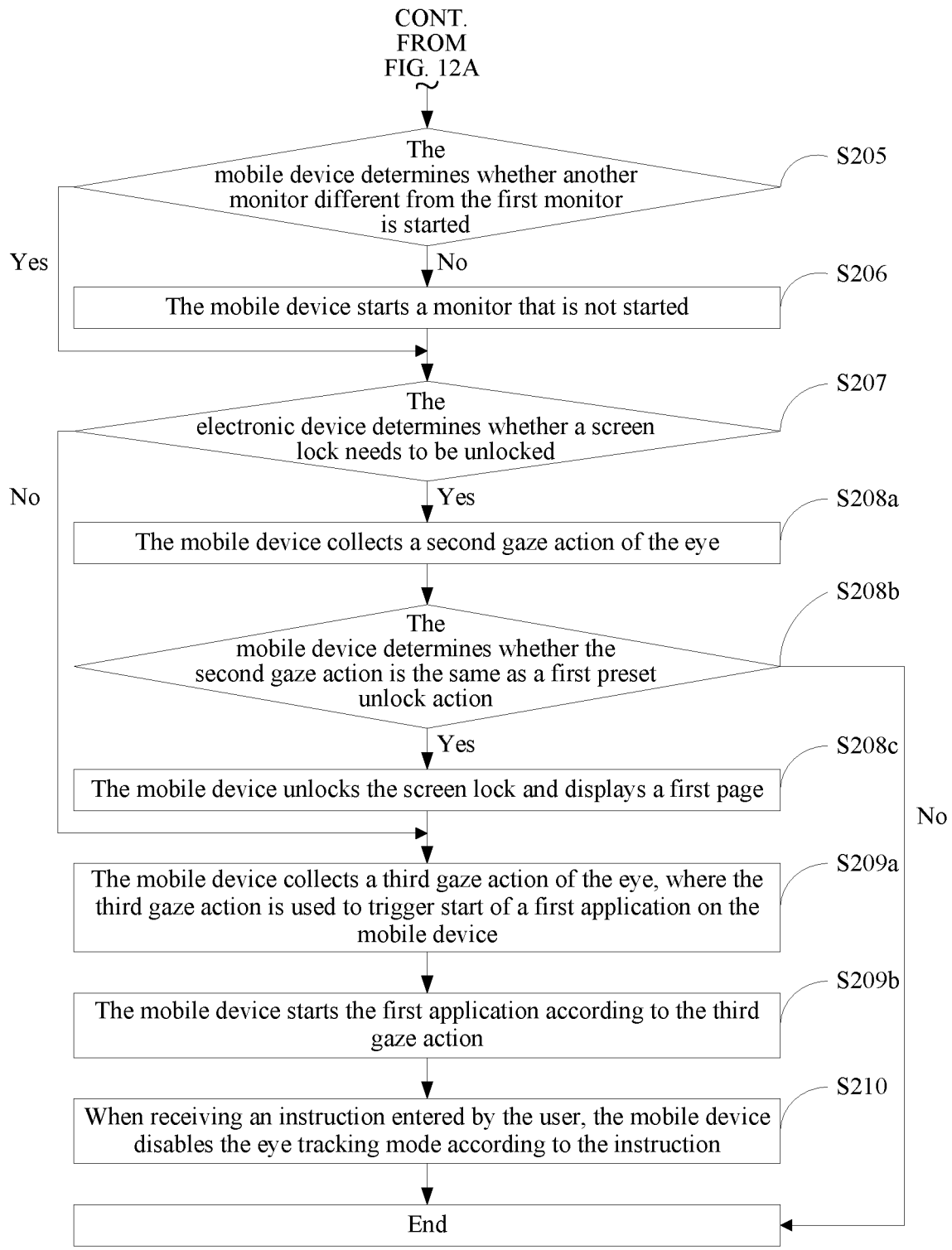
Figure 13A:
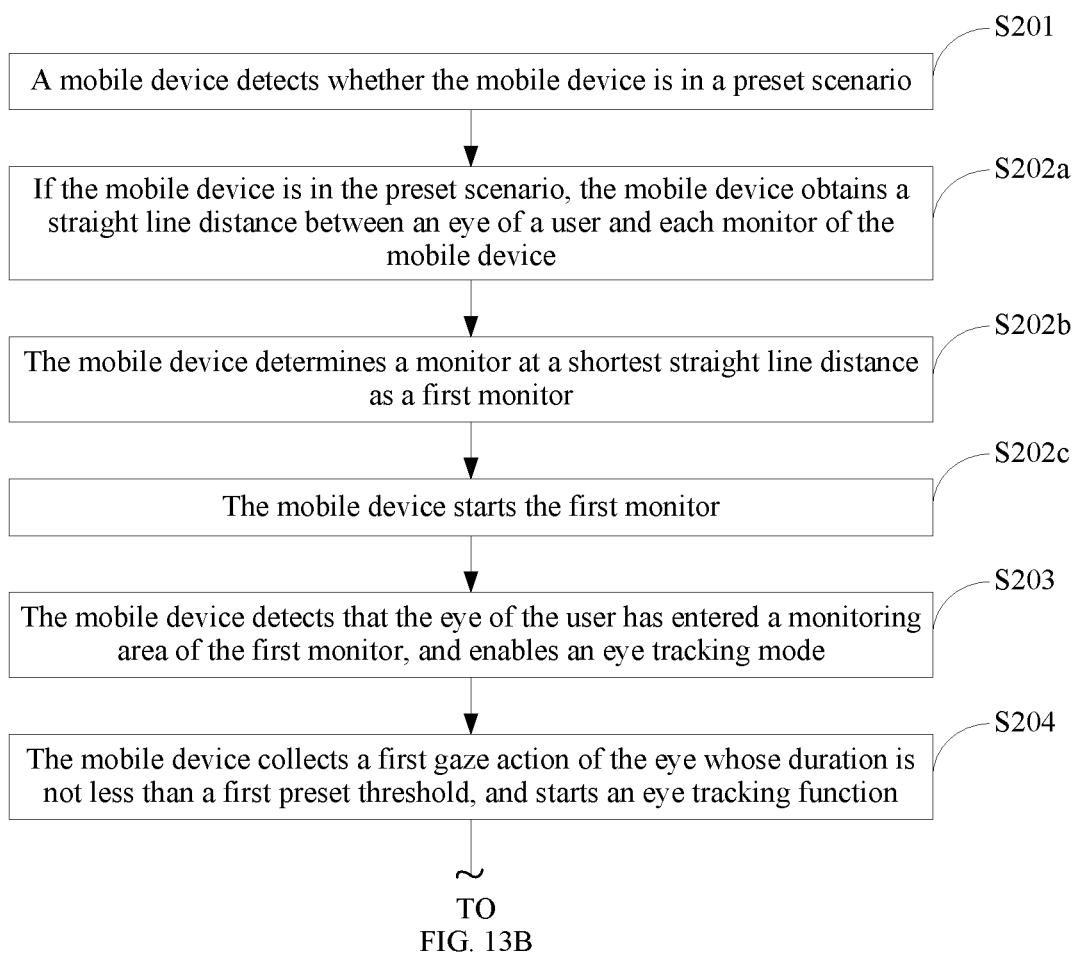
FIG. 13A and FIG. 13B are a ninth schematic flowchart of a method for starting an eye tracking function according to an embodiment of the present disclosure.
Figure 13B:
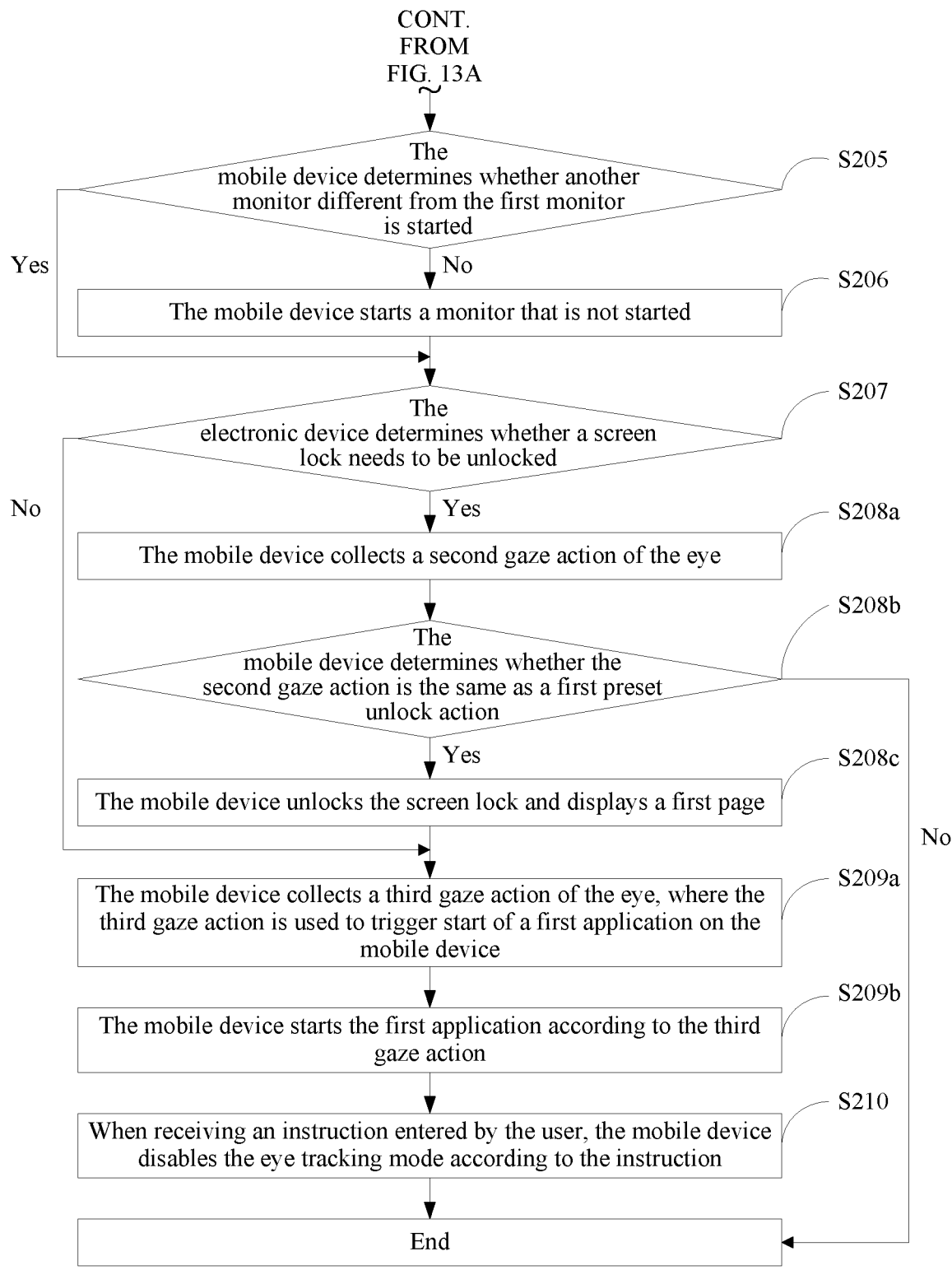

Further, in this application scenario, as shown in FIG. 12B or FIG. 13B, step S209 may be replaced with steps S209a and S209b.

Step S209a: The mobile device collects a third gaze action of the eye, where the third gaze action is used to trigger start of an application on the mobile device.

The third gaze action is an action that the eye gazes at the at least one monitor, and the third gaze action is different from the second gaze action.

Optionally, the third gaze action may be an action that the eye gazes at the at least one monitor device, or may be an action that the eye gazes at a track area of the at least one monitor.

Further, the third gaze action may be an action that the eye gazes at one of the at least one monitor, or may be an action combination of sequential gazes of the eye at a plurality of monitor devices of the at least one monitor.

Further, the third gaze action may be an action that the eye gazes at a track area of one of the at least one monitor, or may be an action combination of gazes of the eye at track areas of a plurality of monitors of the at least one monitor.

In an embodiment, because a monitor device is relatively small-sized, an eye gaze of a user is not definitely accurate. In this scenario, preferably, the mobile device may determine a gaze of the eye at a specific area near the monitor device as a gaze of the user at the monitor device.

For example, a gaze of a user at an area inside a circle whose center is a front-facing camera of a mobile phone and whose radius is one centimeter may be considered as a gaze action that the user is gazing at a monitor device.

It is easy to understood that track areas of a plurality of monitors of the at least one monitor may overlap. In this scenario, preferably, the mobile device includes a position at which the eye gazes into a track area of a monitor at a shortest straight line distance from the position.

For example, the third gaze action is a gaze of the eye at the first area, and a wink frequency of an individual eye within a preset time is equal to a fourth preset threshold.

For example, the third gaze action is sequential gazes of the eye at the first area, a third area, and the fourth area.

It should be noted that the mobile device may collect the third gaze action of the eye using all started monitors, or may collect the third gaze action of the eye using a monitor matching the third gaze action.

When being an action combination of gazes of the eye at a plurality of monitor devices of the at least one monitor, or an action combination of gazes of the eye at track areas of a plurality of monitors of the at least one monitor, the third gaze action is a combination of actions completed within a specific preset time.

For example, when the user completes actions of gazing at a first sensor, a third sensor, and a second sensor continuously in sequence within five seconds, a particular predetermined application is started.

It can be understood that in a scenario in which the mobile device collects the third gaze action of the eye using all the started monitors, the third gaze action collected by the mobile device is more accurate.

Step S209b: The mobile device starts the application according to the third gaze action.

The third gaze action is used to trigger start of an application on the mobile device. Therefore, after the mobile device collects the third gaze action of the eye using the first monitor, the mobile device can rapidly start the application.

It can be learned from the foregoing description that the mobile device in this embodiment of the present disclosure can start the application after collecting the third gaze action of the eye, and the user no longer needs to use the eye to gaze at the mobile device for a long time. Moreover, the user cannot use the eye to interact with the mobile device before the eye tracking cursor appears on the display of the mobile device. This reduces time of interaction between the user and the mobile device and brings convenience to the user, improving user experience.

Further, in the method for starting an eye tracking function provided in this embodiment of the present disclosure, after the mobile device starts the application, the mobile device may further collect a close action of the eye, and implement disabling of the eye tracking mode according to the close action. The close action is used to trigger disabling of the eye tracking mode. Compared with that in the other approaches, the method provided in this embodiment of the present disclosure enables the user to disable the eye tracking mode using only the eye. This brings convenience to the user, and can reduce power consumption of the mobile device.

Figure 14A:
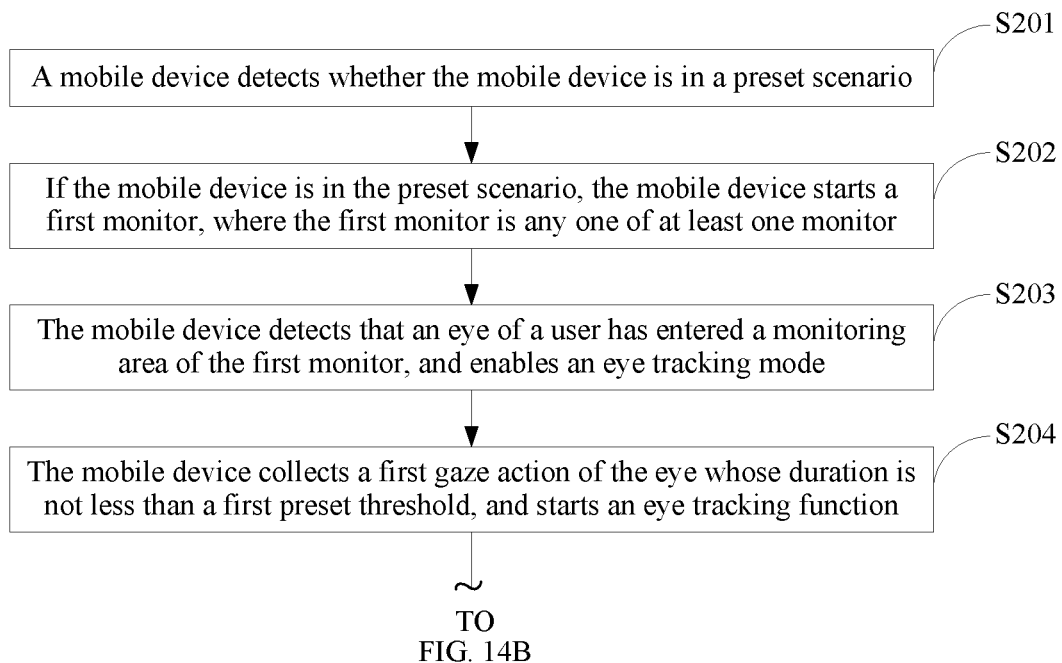
FIG. 14A and FIG. 14B are a tenth schematic flowchart of a method for starting an eye tracking function according to an embodiment of the present disclosure.
Figure 14B:
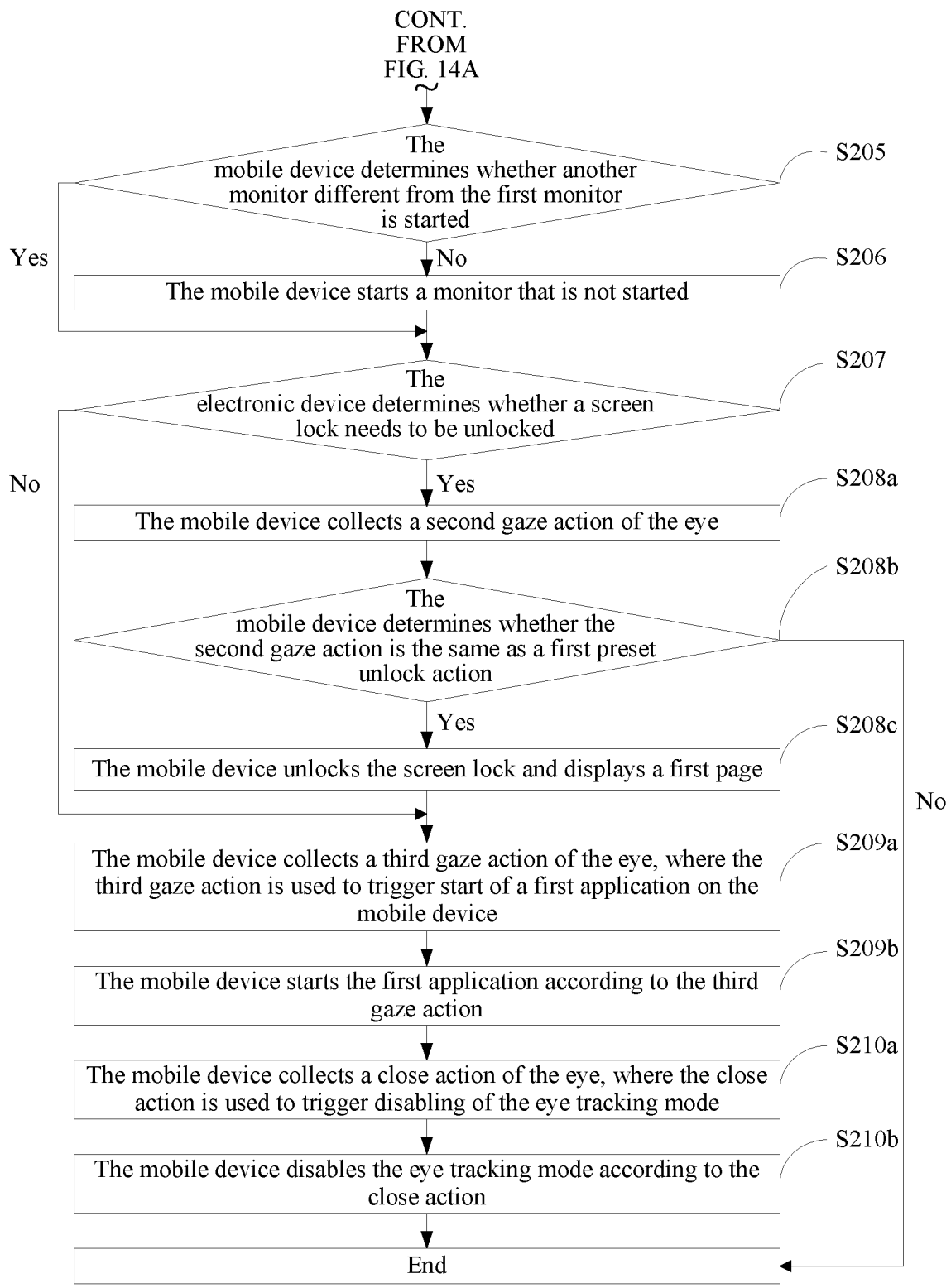
Figure 15A:
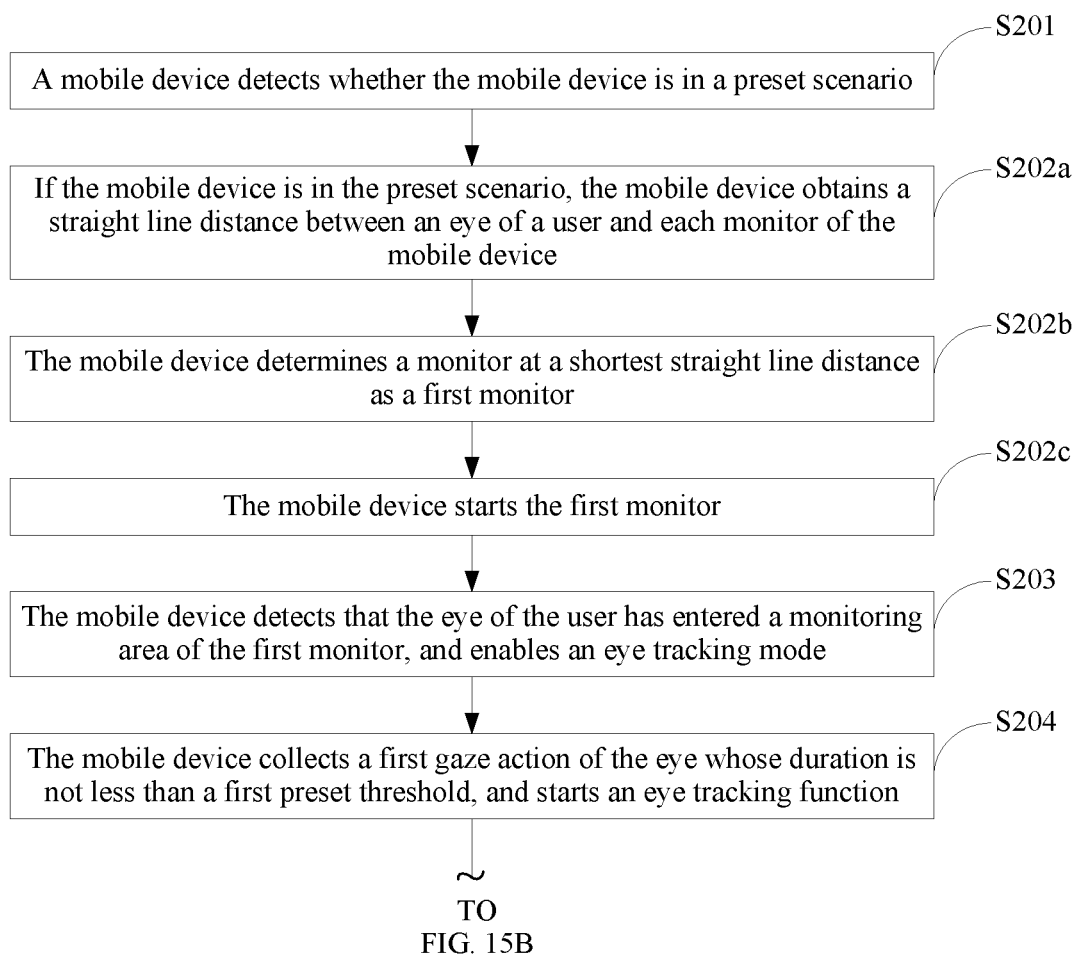
FIG. 15A and FIG. 15B are an eleventh schematic flowchart of a method for starting an eye tracking function according to an embodiment of the present disclosure.
Figure 15B:
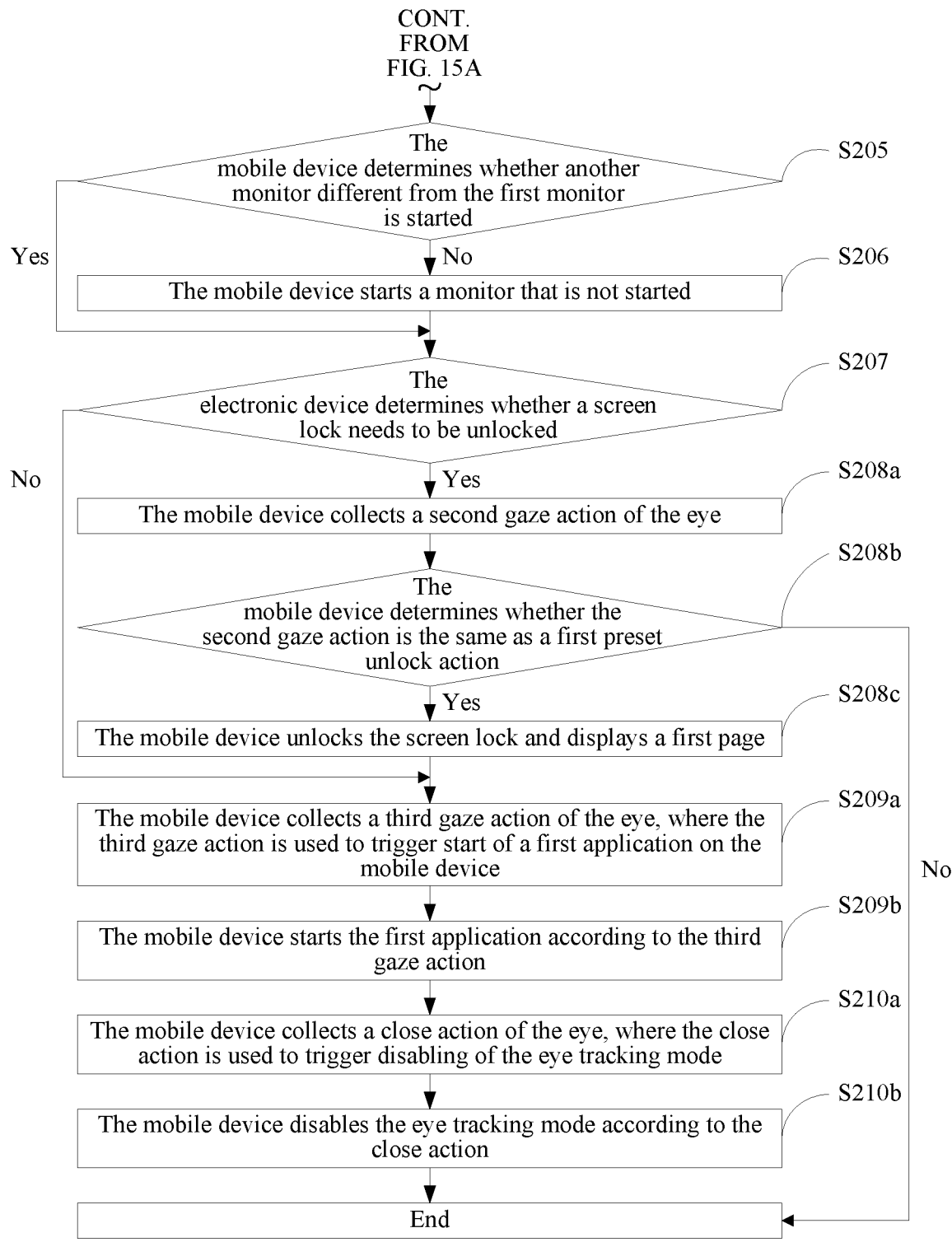

Further, as shown in FIG. 14B or FIG. 15B, step S210 in this embodiment of the present disclosure may be replaced with steps S210a and S210b.

Step S210a: The mobile device collects a close action of the eye, where the close action is used to trigger disabling of the eye tracking mode.

The close action is an action that the eye gazes at the at least one monitor.

Optionally, the close action may be an action that the eye gazes at the at least one monitor device, or may be an action that the eye gazes at a track area of the at least one monitor. In this embodiment of the present disclosure, information about the close action is not limited.

Further, the close action may be an action that the eye gazes at one of the at least one monitor, or may be an action combination of sequential gazes of the eye at a plurality of monitor devices of the at least one monitor.

Further, the close action may be an action that the eye gazes at a track area of one of the at least one monitor, or may be an action combination of gazes of the eye at track areas of a plurality of monitors of the at least one monitor.

In actual application, because a monitor device is relatively small-sized, an eye gaze of a user is not definitely accurate. In this scenario, preferably, the mobile device may determine a gaze of the eye at a specific area near the monitor device as a gaze of the user at the monitor device.

For example, a gaze of a user at an area inside a circle whose center is a front-facing camera of a mobile phone and whose radius is one centimeter may be considered as a gaze action that the user is gazing at a monitor device.

Track areas of a plurality of monitors of the at least one monitor may overlap. Preferably, in this scenario, the mobile device includes a position at which the eye gazes into a track area of a monitor at a shortest straight line distance from the position.

For example, the close action in this embodiment of the present disclosure is sequential gazes of the eye at the first area, the fourth area, and the second area.

It should be noted that the mobile device may collect the close action of the eye using all started monitors, or may collect the close action of the eye using a monitor matching the close action.

In a scenario in which the mobile device collects the close action of the eye using all the started monitors, the close action collected by the mobile device is more accurate.

Step S210b: The mobile device disables the eye tracking mode according to the close action.

That the mobile device disables the eye tracking mode may be that the mobile device turns off the display and disables the eye tracking mode, or may be that the mobile device disables only the eye tracking mode without changing the display of the mobile device.

For example, the close action in this embodiment of the present disclosure is sequential gazes of the eye at the first area, the fourth area, and the second area. When the user gazes at the first area, the fourth area, and the second area in sequence, the mobile device recognizes that this action is a close action, and the mobile device disables the eye tracking mode.

It can be learned from the foregoing description that the mobile device in this embodiment of the present disclosure can disable the eye tracking mode after obtaining the close action of the eye, and the user does not need to stop the eye tracking function manually. This reduces manual operations by the user and brings convenience to the user. In addition, this resolves a problem of large power consumption of a mobile device that is caused if a user forgets to disable an eye tracking mode, and reduces power consumption of the mobile device.

This embodiment of the present disclosure provides a method for starting an eye tracking function, and the method is applied to a mobile device having an eye tracking function. When determining that the mobile device is in a preset scenario, the mobile device starts a first monitor, and when detecting that an eye of a user has entered a monitoring area of the first monitor, the mobile device enables an eye tracking mode. After the eye tracking mode is enabled, if the mobile device collects a first gaze action of the eye whose duration is not less than a first preset threshold, the mobile device starts the eye tracking function.

According to this solution, in a condition of the preset scenario, the mobile device can enable the eye tracking mode when detecting, using the first monitor, that the eye of the user has entered the monitoring area of the first monitor. Further, after the eye tracking mode is enabled, if the mobile device collects, using the first monitor, the first gaze action of the eye whose duration is not less than the first preset threshold, the mobile device starts the eye tracking function. This avoids a problem of poor convenience that, in the condition of the preset scenario, a user cannot use, before the user starts an eye tracking function manually, the eye tracking function of a mobile device to complete a related service. The present disclosure implements that the mobile device starts by itself the eye tracking function, making it more convenient for the user to use the mobile device.

Embodiment 4

Figure 16:
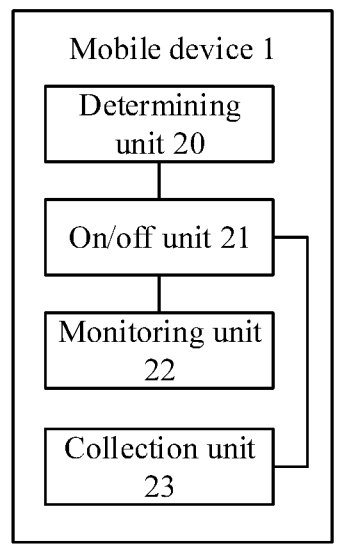
FIG. 16 is a third schematic structural diagram of a mobile device according to an embodiment of the present disclosure.

This embodiment of the present disclosure provides a mobile device 1. As shown in FIG. 16, the mobile device 1 has an eye tracking function, and the mobile device 1 contains at least one monitor. The mobile device 1 includes a determining unit 20, an on/off unit 21, a monitoring unit 22, and a collection unit 23.

The determining unit 20 is configured to determine whether the mobile device 1 is in a preset scenario.

The on/off unit 21 is configured to start at least one monitor when the determining unit 20 determines that the mobile device 1 is in the preset scenario.

The monitoring unit 22 is configured to monitor whether an eye of a user has entered a monitoring area of the at least one monitor.

The on/off unit 21 is further configured to enable an eye tracking mode if the monitoring unit 22 detects that the eye of the user has entered the monitoring area of the at least one monitor.

The collection unit 23 is configured to collect a first gaze action of the eye.

The on/off unit 21 is further configured to start the eye tracking function if the collection unit 23 collects a first gaze action of the eye whose duration is not less than a first preset threshold, where the first gaze action is used to start the eye tracking function.

Figure 17:
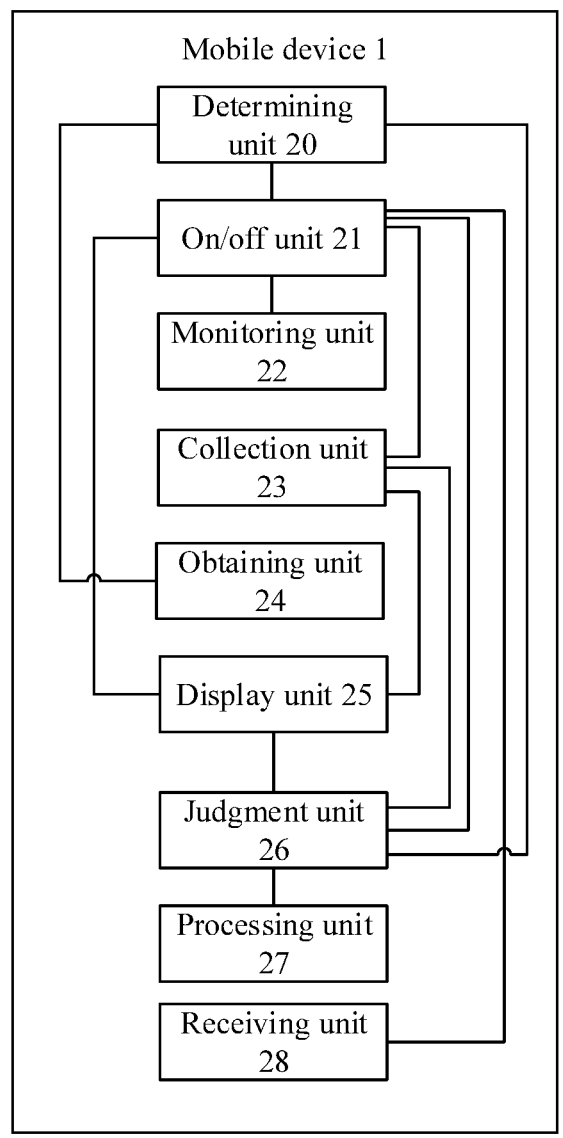
FIG. 17 is a fourth schematic structural diagram of a mobile device according to an embodiment of the present disclosure.

Further, as shown in FIG. 17, the mobile device 1 further includes an obtaining unit 24.

The obtaining unit 24 is configured to obtain a straight line distance between the eye and each monitor of the mobile device 1.

Further, the determining unit 20 is further configured to determine a monitor at a shortest straight line distance obtained by the obtaining unit 24, as a to-be-started monitor.

Further, as shown in FIG. 17, the mobile device 1 further includes a display unit 25.

The display unit 25 is configured to display an interaction screen after the on/off unit 21 starts the eye tracking function.

The on/off unit 21 is further configured to start a monitor that is not started before the display unit 25 displays the interaction screen.

Further, as shown in FIG. 17, the mobile device 1 further includes a judgment unit 26.

The judgment unit 26 is configured to determine whether a screen lock needs to be unlocked after the on/off unit 21 starts the monitor that is not started and before the display unit 25 displays the interaction screen.

The display unit 25 is further configured to display a lock screen if the judgment unit 26 determines that the screen lock needs to be unlocked.

The collection unit 23 is further configured to collect a second gaze action of the eye.

The judgment unit 26 is further configured to determine whether the second gaze action collected by the collection unit 23 is the same as a first preset unlock action.

Further, the mobile device 1 further includes a processing unit 27.

The processing unit 27 is configured to unlock the screen lock if the judgment unit 26 determines that the second gaze action is the same as the first preset unlock action.

The judgment unit 26 is further configured to determine whether the mobile device 1 is in a secure state, where the secure state means that geographical location information of the mobile device 1 is the same as preset geographical location information, or that a distance between the mobile device 1 and a wearable device is not greater than a second preset threshold and a wireless connection has been established between the wearable device and the mobile device 1.

The determining unit 20 is further configured to determine that the screen lock does not need to be unlocked if the judgment unit 26 determines that the mobile device 1 is in the secure state.

The collection unit 23 is further configured to collect a third gaze action of the eye after the display unit 25 displays the interaction screen, where the third gaze action is used to trigger start of an application on the mobile device 1.

The on/off unit 21 is further configured to start the application according to the third gaze action collected by the collection unit 23.

The collection unit 23 is further configured to collect a close action of the eye after the on/off unit 21 starts the application, where the close action is used to trigger disabling of the eye tracking mode.

The on/off unit 21 is further configured to disable the eye tracking mode according to the close action collected by the collection unit 23.

Further, as shown in FIG. 17, the mobile device 1 further includes a receiving unit 28.

The receiving unit 28 is configured to receive an instruction entered by the user.

The on/off unit 21 is further configured to disable the eye tracking mode according to the instruction received by the receiving unit 28.

Further, the preset scenario is a scenario in which the mobile device 1 receives a notification message in a screen off state, a scenario in which the mobile device 1 is laid flat and receives no operation, or a scenario in which the user wakes up the mobile device 1 using voice.

This embodiment of the present disclosure provides a mobile device 1, including a determining unit 20, an on/off unit 21, a monitoring unit 22, and a collection unit 23. When the mobile device 1 is in a preset scenario, the mobile device 1 starts at least one monitor, and when detecting that an eye of a user has entered a monitoring area of the at least one monitor, the mobile device 1 enables an eye tracking mode. After the eye tracking mode is enabled, if the mobile device 1 collects a first gaze action of the eye whose duration is not less than a first preset threshold, the mobile device 1 starts an eye tracking function.

According to this solution, in a condition of the preset scenario, the mobile device 1 can enable the eye tracking mode when detecting, using the at least one monitor, that the eye of the user has entered the monitoring area of the at least one monitor. Further, after the eye tracking mode is enabled, if the mobile device 1 collects, using the at least one monitor, the first gaze action of the eye whose duration is not less than the first preset threshold, the mobile device starts the eye tracking function. This avoids a problem of poor convenience that, in the condition of the preset scenario, a user cannot use, before the user starts an eye tracking function manually, the eye tracking function of a mobile device to complete a related service. The present disclosure implements that the mobile device starts by itself the eye tracking function, making it more convenient for the user to use the mobile device.

Embodiment 5

This embodiment of the present disclosure provides a readable storage medium, including one or more programs. When the mobile device executes the one or more programs, the mobile device performs steps described in Embodiment 2 or Embodiment 3.

It may be clearly understood by a person skilled in the art that, for the purpose of convenient and brief description, the foregoing division of function modules is used as an example for illustration. In actual application, the foregoing functions can be distributed to and implemented by different function modules according to a requirement, that is, an inner structure of a mobile device is divided into different function modules to implement all or some of the functions described above. For a detailed working process of the foregoing system, mobile device, and unit, reference may be made to a corresponding process in the foregoing method embodiments, and details are not described herein any further.

In the several embodiments provided in this application, it should be understood that the disclosed system, mobile device, and method may be implemented in other manners. For example, the described mobile device embodiment is merely an example. For example, the module or unit division is merely logical function division and may be other division during actual implementation. For example, a plurality of units or components may be combined or integrated into another system, or some features may be ignored or not performed. In addition, the displayed or discussed mutual couplings or direct couplings or communication connections may be indirect couplings or communication connections via some interfaces, mobile devices, or units, and may be implemented in electrical, mechanical, or other forms.

The units described as separate parts may or may not be physically separate. Parts displayed as units may or may not be physical units, and may be located in one position or distributed on a plurality of network units. Some or all of the units may be selected according to actual requirements to achieve the objectives of the solutions of the embodiments.

In addition, functional units in the embodiments of the present disclosure may be integrated into one processing unit, or each of the units may exist alone physically, or two or more units are integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions of the present disclosure essentially, or the part contributing to the other approaches, or all or a part of the technical solutions may be implemented in the form of a software product. The software product is stored in a storage medium and includes several instructions for instructing a computer device (which may be a personal computer, a server, or a network device) or a processor (a processor) to perform all or a part of the steps of the methods described in the embodiments of the present disclosure. The foregoing storage medium includes any medium that can store program code, such as a universal serial bus (USB) flash drive, a removable hard disk, a read-only memory (ROM), a RAM, a magnetic disk, or an optical disc.

The foregoing descriptions are merely specific implementations of the present disclosure, but are not intended to limit the protection scope of the present disclosure. Any variation or replacement readily figured out by a person skilled in the art within the technical scope disclosed in the present disclosure shall fall within the protection scope of the present disclosure. Therefore, the protection scope of the present disclosure shall be subject to the protection scope of the claims.

What is claimed is:

1. A method for starting an eye tracking function, applied to a mobile device having the eye tracking function, comprising:
  determining that the mobile device is in a preset scenario;
  starting at least one monitor when the mobile device is in the preset scenario;
  detecting that an eye of a user has entered a monitoring area of the at least one monitor;
  enabling an eye tracking mode;
  determining that a screen lock of the mobile device does not need to be unlocked;
  collecting a first gaze action of the eye whose duration is not less than a first preset threshold; and
  starting the eye tracking function, wherein the first gaze action starts the eye tracking function.

2. The method according to claim 1, wherein before starting the at least one monitor, the method further comprises:
  obtaining a straight line distance between the eye and each monitor of the mobile device; and
  selecting a monitor that has a shortest straight line distance to be a to-be-started monitor.

3. The method according to claim 1, wherein after starting the eye tracking function, the method further comprises displaying an interaction screen.

4. The method according to claim 3, wherein before displaying the interaction screen, the method further comprises starting a monitor that is not started.

5. The method according to claim 4, wherein after starting the monitor that is not started and before displaying the interaction screen, the method further comprises:
  determining whether the screen lock needs to be unlocked;
  displaying a lock screen when the screen lock needs to be unlocked;
  collecting a second gaze action of the eye; and unlocking the screen lock when the second gaze action is the same as a preset unlock action.

6. The method according to claim 3, wherein after displaying the interaction screen, the method further comprises:
collecting a third gaze action of the eye, wherein the third gaze action triggers start of an application on the mobile device; and
starting the application according to the third gaze action.

7. The method according to claim 6, wherein after starting the application, the method further comprises:
collecting a close action of the eye, wherein the close action triggers disabling of the eye tracking mode; and
disabling the eye tracking mode according to the close action, wherein disabling the eye tracking mode comprises turning off the mobile device or disabling only the eye tracking mode without changing a display of the mobile device.

8. The method according to claim 6, wherein after starting the application, the method further comprises:
receiving an instruction from the user; and
disabling the eye tracking mode according to the instruction.

9. The method according to claim 1, wherein the mobile device is in a secure state, wherein the secure state comprises that either geographical location information of the mobile device is the same as preset geographical location information or a distance between the mobile device and a wearable device is not greater than a second preset threshold, and wherein a wireless connection has been established between the wearable device and the mobile device.

10. The method according to claim 1, wherein the preset scenario comprises a scenario in which the mobile device receives a notification message in a screen off state, a scenario in which the mobile device is laid flat and receives no operation, or a scenario in which the user wakes up the mobile device using voice.

11. A mobile device, wherein the mobile device has an eye tracking function, and wherein the mobile device comprises:
a monitor; and
a processor coupled to the at least one monitor and configured to:
determine that the mobile device is in a preset scenario, wherein the preset scenario comprises a first scenario in which the mobile device receives a notification message in a screen off state, a second scenario in which the mobile device is laid flat and receives no operation, or a third scenario in which a user wakes up the mobile device using voice;
start the monitor when the mobile device is in the preset scenario;
detect that an eye of the user has entered a monitoring area of the monitor;
enable an eye tracking mode;
collect a first gaze action of the eye whose duration is not less than a first preset threshold; and
start the eye tracking function, wherein the first gaze action starts the eye tracking function.

12. The mobile device according to claim 11, wherein the mobile device further comprises a display coupled to the processor and configured to display an interaction screen after the processor starts the eye tracking function.

13. The mobile device according to claim 12, wherein before the display displays the interaction screen, the processor is further configured to start one of the monitor that is not started.

14. The mobile device according to claim 13, wherein the processor is further configured to:

determine whether a screen lock needs to be unlocked after starting the monitor that is not started and before the display displays the interaction screen;
determine that the screen lock needs to be unlocked;
trigger the display to display a lock screen when the screen lock needs to be unlocked;
collect a second gaze action of the eye;
determine whether the second gaze action is the same as a first preset unlock action; and
unlock the screen lock when the second gaze action is the same as the first preset unlock action.

15. The mobile device according to claim 14, wherein the processor is further configured to:
determine whether the mobile device is in a secure state, wherein the secure state comprises that either geographical location information of the mobile device is the same as preset geographical location information or a distance between the mobile device and a wearable device is not greater than a second preset threshold, and wherein a wireless connection has been established between the wearable device and the mobile device; and
determine that the screen lock does not need to be unlocked when the mobile device is in the secure state.

16. The mobile device according to claim 12, wherein the processor is further configured to:
collect a third gaze action of the eye after the display displays the interaction screen, wherein the third gaze action triggers start of an application on the mobile device; and
start the application according to the third gaze action.

17. The mobile device according to claim 16, wherein the processor is further configured to:
collect a close action of the eye after starting the application, wherein the close action triggers disabling of the eye tracking mode; and
disable the eye tracking mode according to the close action, wherein disabling the eye tracking mode comprises turning off the mobile device or disabling only the eye tracking mode without changing a display of the mobile device.

18. The mobile device according to claim 16, wherein the processor is further configured to:
receive an instruction from the user; and
disable the eye tracking mode according to the received instruction.

19. A mobile device, wherein the mobile device has an eye tracking function, and wherein the mobile device comprises:
a plurality of monitors, wherein the monitors comprise an infrared sensor; and
processor coupled to the monitors and configured to:
determine that the mobile device is in a preset scenario;
obtain, by an infrared sensor measurement from the infrared sensor, a straight line distance between an eye and each monitor of the mobile device;
select one of the monitors that has a shortest straight line distance to be a to-be-started monitor;
start the to-be-started monitor when the mobile device is in the preset scenario;
detect that an eye of a user has entered a monitoring area of the to-be-started monitor;
enable an eye tracking mode;
collect a first gaze action of the eye whose duration is not less than a first preset threshold; and
start the eye tracking function, wherein the first gaze action starts the eye tracking function.

20. The mobile device according to claim 19, wherein the preset scenario comprises a scenario in which the mobile device receives a notification message in a screen off state, a scenario in which the mobile device is laid flat and receives no operation, or a scenario in which the user wakes up the mobile device using voice.

\* \* \* \* \*